US006344353B1

(12) United States Patent
Ye et al.

(10) Patent No.: US 6,344,353 B1
(45) Date of Patent: Feb. 5, 2002

(54) ISOLATED HUMAN PROTEASE PROTEINS, NUCLEIC ACID MOLECULES ENCODING HUMAN PROTEASE PROTEINS, AND USES THEREOF

(75) Inventors: Jane Ye, Boyds; Valentina Di Francesco, Rockville; Ellen M. Beasley, Darnestown, all of MD (US)

(73) Assignee: PE Corporation (NY), Norwalk, CT (US)

( * ) Notice: Subject to any disclaimer, the term of this patent is extended or adjusted under 35 U.S.C. 154(b) by 0 days.

(21) Appl. No.: 09/740,035

(22) Filed: Dec. 20, 2000

(51) Int. Cl.[7] .......................... C12N 15/57

(52) U.S. Cl. .......................... 435/226; 435/6; 435/252.3; 435/320.1; 536/23.2

(58) Field of Search .......................... 435/6, 252.3, 226, 435/320.1; 536/23.2

*Primary Examiner*—Charles L. Patterson, Jr.
(74) *Attorney, Agent, or Firm*—Celera Genomics; Robert A. Millman; Justin D. Karjala

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

10 Claims, 25 Drawing Sheets

```
   1 GCCATGGTGG GGCAGAGGTT GGGAAGATGG CGTGGCGAGG CTGGGCGCAG
  51 AGAGGCTGGG GCTGCGGCCA GGCGTGGGGT GCGTCGGTGG GCGGCCGCAG
 101 CTGCGAGGAG CTCACTGCGG TCCTAACCCC GCCGCAGCTC CTCGGACGCA
 151 GGTTTAACTT CTTTATTCAA CAAAAATGCG GATTCAGAAA AGCACCCAGG
 201 AAGGTTGAAC CTCGAAGATC AGACCCAGGG ACAAGTGGTG AAGCATACAA
 251 GAGAAGTGCT TTGATTCCTC CTGTGGAAGA AACAGTCTTT TATCCTTCTC
 301 CCTATCCTAT AAGGAGTCTC ATAAAACCTT TATTTTTTAC TGTTGGGTTT
 351 ACAGGCTGTG CATTTGGATC AGCTGCTATT TGGCAATATG AATCACTGAA
 401 ATCCAGGGTC CAGAGTTATT TTGATGGTAT AAAAGCTGAT TGGTTGGATA
 451 GCATAAGACC ACAAAAAGAA GGAGACTTCA GAAAGGAGAT TAACAAGTGG
 501 TGGAATAACC TAAGTGATGG CCAGCGGACT GTGACAGGTA TTATAGCTGC
 551 AAATGTCCTT GTATTCTGTT TATGGAGAGT ACCTTCTCTG CAGCGGACAA
 601 TGATCAGATA TTTCACATCG AATCCAGCCT CAAGTGTTAT TTCCAATTTT
 651 GTCAGTTACG TGGGTAAAGT TGCCACAGGA AGATATGGAC CATCACTTGG
 701 TGCATCTGGT GCCATCATGA CAGTCCTCGC AGCTGTCTGC ACTAAGATCC
 751 CAGAAGGGAG GCTTGCCATT ATTTTCCTTC CGATGTTCAC GTTCACAGCA
 801 GGGAATGCCC TGAAAGCCAT TATCGCCATG GATACAGCAG GAATGATCCT
 851 GGGATGGAAA TTTTTTGATC ATGCGGCACA TCTTGGGGGA GCTCTTTTTG
 901 GAATATGGTA TGTTACTTAC GGTCATGAAC TGATTTGGAA GAACAGGGAG
 951 CCGCTAGTGA AAATCTGGCA TGAAATAAGG ACTAATGGCC CCAAAAAAGG
1001 AGGTGGCTCT AAGTAAAACT GGGATTGGAC AGTAGTGGTG CATCTGGTCC
1051 TTGCCGCCTG AGAGCCCCAG GAGACATCGG CTAGAGTGAC CATGGCTATG
1101 CTCCCGTCTG GAAGATGCCA GCATCTGGCC TCCCACTGTT TTCAGCTGTG
1151 TCCCCCAGTC CGTGTCTTTT TAGAATGTGA ATGATGATAA AGTTGTGAAA
1201 TAAAGGTTTC TATCTAGTTT GTAAAAAAAA AAAAAAAAAA AAAAAAA (SEQ ID NO:1)
```

FEATURES:
5'UTR: 1 - 26
Start Codon: 27
Stop Codon: 1014
3'UTR: 1017

Homologous proteins:

| | | |
|---|---|---|
| gi\|11066250\|gb\|AAG28519.1\|AF197937_1 (AF197937) presenilins int... | 668 | 0.0 |
| gi\|8924134\|ref\|NP_061092.1\| hypothetical protein PRO2207 [Homo ... | 264 | 1e-69 |
| gi\|7303544\|gb\|AAF58598.1\| (AE003824) CG8972 gene product [Droso... | 186 | 4e-46 |
| gi\|3219925\|sp\|014364\|YB4J_SCHPO HYPOTHETICAL 33.6 KD PROTEIN C3... | 69 | 1e-10 |
| gi\|6321538\|ref\|NP_011615.1\| Ygr101wp [Saccharomyces cerevisiae]... | 64 | 3e-09 |

FIGURE 1A

EST:

| | | |
|---|---|---|
| gi\|10216540 /dataset=dbest /taxon=96... | 1203 | 0.0 |
| gi\|10215044 /dataset=dbest /taxon=96... | 1203 | 0.0 |
| gi\|10212049 /dataset=dbest /taxon=96... | 1172 | 0.0 |
| gi\|10154606 /dataset=dbest /taxon=96... | 1160 | 0.0 |
| gi\|9141009 /dataset=dbest /taxon=9606... | 1144 | 0.0 |
| gi\|9338606 /dataset=dbest /taxon=960... | 1094 | 0.0 |
| gi\|9720819 /dataset=dbest /taxon=960... | 1090 | 0.0 |
| gi\|5857747 /dataset=dbest /taxon=9606 ... | 1033 | 0.0 |
| gi\|10813749 /dataset=dbest /taxon=960... | 1009 | 0.0 |

EXPRESSION INFORMATION FOR MODULATORY USE:
gi|10216540 Lung
gi|10215044 Lung small cell carcinoma
gi|10212049 Lung small cell carcinoma
gi|10154606 Ovary adenocarcinoma
gi|9141009 Lung
gi|9338606 Uterus endometrium
gi|9720819 Lymph Burkitt lymphoma
gi|5857747 Colon
gi|10813749 Dendritic cells Tissue Expression:
Human leukocytes

FIGURE 1B

```
  1 MAWRGWAQRG WGCGQAWGAS VGGRSCEELT AVLTPPQLLG RRFNFFIQQK
 51 CGFRKAPRKV EPRRSDPGTS GEAYKRSALI PPVEETVFYP SPYPIRSLIK
101 PLFFTVGFTG CAFGSAAIWQ YESLKSRVQS YFDGIKADWL DSIRPQKEGD
151 FRKEINKWWN NLSDGQRTVT GIIAANVLVF CLWRVPSLQR TMIRYFTSNP
201 ASSVISNFVS YVGKVATGRY GPSLGASGAI MTVLAAVCTK IPEGRLAIIF
251 LPMFTFTAGN ALKAIIAMDT AGMILGWKFF DHAAHLGGAL FGIWYVTYGH
301 ELIWKNREPL VKIWHEIRTN GPKKGGGSK (SEQ ID NO:2)

FEATURES:
Functional domains and key regions:
Prosite results:
[1] PDOC00001 PS00001 ASN_GLYCOSYLATION
N-glycosylation site

          161-164 NLSD
----------------------------------------------
[2] PDOC00005 PS00005 PKC_PHOSPHO_SITE
Protein kinase C phosphorylation site

Number of matches: 3
     1    123-125 SLK
     2    142-144 SIR
     3    217-219 TGR
-----------------------------------------------
[3] PDOC00006 PS00006 CK2_PHOSPHO_SITE
Casein kinase II phosphorylation site

Number of matches: 3
     1      25-28 SCEE
     2      69-72 TSGE
     3    130-133 SYFD
-----------------------------------------------
[4] PDOC00008 PS00008 MYRISTYL
N-myristoylation site

Number of matches: 10
     1      12-17 GCGQAW
     2      14-19 GQAWGA
     3      18-23 GASVGG
     4      22-27 GGRSCE
     5    110-115 GCAFGS
     6    171-176 GIIAAN
     7    225-230 GASGAI
     8    228-233 GAIMTV
```

FIGURE 2A

```
     9    272-277 GMILGW
    10    288-293 GALFGI
----------------------------------------------------
[5] PDOC00009 PS00009 AMIDATION
Amidation site

              39-42 LGRR

Membrane spanning structure and domains:
Helix Begin   End   Score Certainity
    1   107   127   1.825 Certain
    2   173   193   1.069 Certain
    3   226   246   1.654 Certain
    4   250   270   1.382 Certain
    5   288   308   1.123 Certain

BLAST Alignment to Top Hit:
Alignment to top blast hit:
>gi|11066250|gb|AAG28519.1|AF197937_1 (AF197937) presenilins
            interacting rhomboid-like protease [Homo sapiens]
          Length = 379

 Score =  668 bits (1706), Expect = 0.0
 Identities = 327/379 (86%), Positives = 328/379 (86%), Gaps = 50/379 (13%)
 Frame = +3

Query: 27   MAWRGWAQRGWGCGQAWGASVGGRSCEELTAVLTPPQLLGRRFNFFIQQKCGFRKAPRKV 206
            MAWRGWAQRGWGCGQAWGASVGGRSCEELTAVLTPPQLLGRRFNFFIQQKCGFRKAPRKV
Sbjct: 1    MAWRGWAQRGWGCGQAWGASVGGRSCEELTAVLTPPQLLGRRFNFFIQQKCGFRKAPRKV 60

Query: 207  EPRRSDPGTSGEAYKRSALIPPVEETVFYPSPYPIRSLIKPLFFTVGFTGCAFGSAAIWQ 386
            EPRRSDPGTSGEAYKRSALIPPVEETVFYPSPYPIRSLIKPLFFTVGFTGCAFGSAAIWQ
Sbjct: 61   EPRRSDPGTSGEAYKRSALIPPVEETVFYPSPYPIRSLIKPLFFTVGFTGCAFGSAAIWQ 120

Query: 387  YESLKSRVQSYFDGIKADWLDSIRPQKEGDFRKEINKWWNNLSDGQRTVTGIIAANVLVF 566
            YESLKSRVQSYFDGIKADWLDSIRPQKEGDFRKEINKWWNNLSDGQRTVTGIIAANVLVF
Sbjct: 121  YESLKSRVQSYFDGIKADWLDSIRPQKEGDFRKEINKWWNNLSDGQRTVTGIIAANVLVF 180

Query: 567  CLWRVPSLQRTMIRYFTSNPAS---------------------------------------- 632
            CLWRVPSLQRTMIRYFTSNPAS
Sbjct: 181  CLWRVPSLQRTMIRYFTSNPASKVLCSPMLLSTFSHFSLFHMAANMYVLWSFSSSIVNIL 240

Query: 633  ------------SVISNFVSYVGKVATGRYGPSLGASGAIMTVLAAVCTKIPEGRLAIIF 776
                         VISNFVSY+GKVATGRYGPSLGASGAIMTVLAAVCTKIPEGRLAIIF
Sbjct: 241  GQEQFMAVYLSAGVISNFVSYLGKVATGRYGPSLGASGAIMTVLAAVCTKIPEGRLAIIF 300
```

FIGURE 2B

```
Query: 777  LPMFTFTAGNALKAIIAMDTAGMILGWKFFDHAAHLGGALFGIWYVTYGHELIWKNREPL 956
            LPMFTFTAGNALKAIIAMDTAGMILGWKFFDHAAHLGGALFGIWYVTYGHELIWKNREPL
Sbjct: 301  LPMFTFTAGNALKAIIAMDTAGMILGWKFFDHAAHLGGALFGIWYVTYGHELIWKNREPL 360

Query: 957  VKIWHEIRTNGPKKGGGSK 1013
            VKIWHEIRTNGPKKGGGSK
Sbjct: 361  VKIWHEIRTNGPKKGGGSK 379 (SEQ ID NO:4)

Hmmer search results (Pfam):
Scores for sequence family classification (score includes all domains):
Model    Description                                      Score    E-value  N
-------- -----------                                      -----    ------- ---
PF01694  Rhomboid family                                    23.3    1.8e-05   1

Parsed for domains:
Model    Domain  seq-f seq-t    hmm-f hmm-t      score  E-value
-------- ------- ----- -----    ----- -----      -----  -------
PF01694    1/1     201   292 ..    59   147 ..    23.3  1.8e-05
```

FIGURE 2C

```
   1 CGAGGTTTCT TCATGTTGGT CAGGCTGGTC TCGAACTCCC GACCTCAGGT
  51 GATCCGTCCG CCTCAGCCTC CCAAAGTACT GCTGGGATTA CAGACGTGAG
 101 CCACCGCACC CGGCCTTTAT CTTTCATTTT TTTTCATGTA TTTTCCTTTA
 151 TTTTAATCAC TTTATCCAGA AACATATCCT CGTCTTGACA GTGCTGTGGT
 201 GCCTGTGGTT TCCAGAAGCT GGGTGTGCTG TGTGTCTGTG GTTTGAGGAA
 251 GTTGCCCATG GAACTGACAG AGGAAGCAGA GTAGTCGTTG CCATTTTTCA
 301 GCCTAGTAGG CAGGATCAGG GACCCCATCT TGCTCTCTTT GCCTTGAACC
 351 ACAATTAGAA TAAAACACCA AAGCCCTGAC TGATCATGAT CATAGCAATC
 401 CGATCTTTAT GATCATGGCC AGACCATTCT CAGGTCGTCT TTACCCTAAG
 451 ATATCAATCA CTGGGTATGA CAACCTAGAC CTAAGGGTGC ACTCTGGGTA
 501 GTAAAGATGA TTAACTCTCC CAAAGGAATC TAAGGAATCC AGAGCAACAC
 551 GAATCACTGC TCTCTTCCTA TAGGGTAAAC CTCCCAAGAC TCCAGTCCCT
 601 GTGAGGAGGC TCTGCCCGCC TGCCCTTCCC AGGGTTCCAG GCTCCACATT
 651 GGGAGGTGTA CACAGTGCTC TTCGCTCTTC ATTGCCTTGT GTATGATCCC
 701 TTTTCCCATC TTTGCATAAA TGCTGTCCCT CTCACCATCT TTAAAAGAGT
 751 TCTGGGTAAT TATTTACCAA AGGTGGTATA ATGCTGTCAC AGTCCCTGCT
 801 AGTGAGACAT CTGATACAAC TGATGGAATC AGTTCAACAA AATGCAGTAA
 851 AATTTTATTT AATGTACTAC GGAGAAAGAA AAAATGCTAC CAGTTATAAG
 901 ATGCATCCTG ATTTCAGATA TTAAAATGGA AAAAATGTCT TAAGATCTGT
 951 GAAAAATGTA GCTTCCTTTC CCACCTCTCA AGTGGGAGAG CAAAAACTGG
1001 ACAGACTAGA AATGCCAGGG GCTAGCTGAG AACCTTACAG AATGAGCAAC
1051 TGCGGAAGCC ACAGGTAACA CCGAGATGTA GATCAGCTGC CAGGGACAAG
1101 ACAAAGAATG TTTTCTAAAG TAAATCCTCT TACCAGTATG TTATTGAAAT
1151 CAGTCCTTAT TGGCATCGAA GAAGGTGAAA GTGCTACTTG CCTGTTGCCT
1201 ACAGAGACTG GAGGAATGAC AAATGTTTAA ATTATTTTAA TTCAACAAGT
1251 AGAGGAATAC CTGCTATGTG AAGGAGTTGT GGCAATTCAT AAAATTAATA
1301 TATTTTTTGA AGTTTGTAGT TTTCAATAAT AATTTCTTAT CTAAAATGTA
1351 ACAAGTTAAT TATATTATCG AATAAACCTC AATTTCGTAG TACTAACAAC
1401 ATCAACACTT ACAGAAAAAG GAAAGTCACT CAACTCCCAC ATGTAAACAG
1451 ACTTTAGAAG CAGTTGCAGA GGTTTTCTAA ATTATCCCTG AATTCCTATC
1501 ACATGACTAT TTTTCTCAGA CATGTTGACC TTCACCTACA CAGATGACTC
1551 ACATATGTTT CCATAAGCTG GCAGTAAGTT TAAGAAGCAT ACCATGCCCT
1601 GAGGAAAAAG AAGTAATGTT AGCTCTTCTA CTCTTGGCCA AAGAACCTAA
1651 TTCTGTATAT TACTTCTGTC TTTGGTTTGG CTATTATAGA CAATAAATTA
1701 TTGATCTGAT TATAATTGAG AAAAGTAAGC TCTTCTAAAG AAGTAAAATA
1751 TGGATCTAGG GAAAGGAAGT TAGCTCCCAG AGCATTTACA ATTTCCCAGG
1801 AATTCTGTGA CTTTACCAAC CCTAGGCAGT GCTGATACTT TAAAAGCATT
1851 CATTTCACTT GCTTTTTTTT GGCTCACCCC CTATCCCCCA GGTATACAGT
1901 ACTCTTACAT AATTGTGGAA GAATCTTACA AGGGGGTAAT GTAGATCAGA
1951 CTTTCCTGCT TTCATTTTTA ACCTCCCTAA ATTATAAATA TTTATTTTGT
2001 AGGTATTATA GCTGCAAATG TCCTTGTATT CTGTTTATGG AGAGTACCTT
2051 CTCTGCAGCG GACAATGATC AGATATTTCA CATCGAATCC AGCCTCAAGT
2101 AAGTCTAACT TGTGTGAATT TATTTTAAGG TAGAAATAAT ATGAAAGAAA
2151 TATGCTTTAG TTAATGGAAG TGCTGTAAAA AAGACGAATT ACCTATCAAT
2201 AGCTACAAGC AAAATGCAGA GGATAGGCTG TAAGCTCCTT CACTGAGGAC
2251 AGGGACCTCA CCTCTCTTTT TCTTTTTCTT TGTTTTTTTT GAGACGGAGT
```

FIGURE 3A

2301 CTTCCTCTGT TGCCCAGGCT GGAGTGCAGT GGTGCAGTCT TAGCTCACTA
2351 CAACCTCCAC CTCCCAGGTT CAAGTGATTC TCCTGCCTCA GCCTCCCTAG
2401 TAGCTAGGAT TACAGGTGCC CGCCACCACA CCCAGCTAGT TTTTGTATTT
2451 TTAATAGAGA CAGGGTTTCA CCGTGTTGGA TAGGCTGTTC TTGAACACCT
2501 GACCTCAGGT GATCTGCCTG GCTCGGCTGG AGTGCAGTGG CGTGATCTCA
2551 GCTCACTGCA AGCTCCGCCT CCCGGGTTCA TGCCATTCTC CTGCCTCAGC
2601 CTCCTGAGTA GCTGGGACTA CAGGTGCCCG CCACCACGCC CCGCTAATTT
2651 TTTTGTATTT TTAGTAGAGA CGGGGTTTCA ACATGTTAGC CAGGATGGTC
2701 TCGATCTCCT GACCTCGTGA TCCGCCCGCC TCAGCCTCCC AAAGTGCTGG
2751 GATTATAGGC GTGAGCCACT GCGCCCGGCC AATTTACTTT TTATTTTATT
2801 TTATTTTATT TTTTGAGACA GGGTCTTGCT CTGTTGCCCA GGCTAGAGTG
2851 CAGTGATACG ATCTTGGCTC ACTGCAACCT CTGCTTCTCA GGCTCAACTG
2901 ATCCTCCCAC CTCAGCCCCC AGGAGCTGGG ACTACAGGTG CATGCCACCA
2951 TGCCCAGCTA ATTTTTTTTG TTTTTAGTGC AGATGAGGTC TTGCCATGTT
3001 GCCCAGACTG CTTATTTTTT TCTAATCAAC TTTTGCCATA AGGACAAGTT
3051 GCTTTCATTG AACTGAGAGT TTTTATTGGT TGCTTACTAA GTAGAAAAGA
3101 ATATTTATTA AGACAGCTTT TTGTCACTTT TAAAAATGAT GTCTTAAGCT
3151 GGGCATAGTG ACTCACATCT ATAATCCCAG CACTTGGGGA GGCTGAGGCA
3201 GGTGAACTGC TTGAGCTCAG GAGTTCGAGA CCAGCCTGGG AAACATGGTG
3251 AAACCCCATC TCTACTAAAA ATACAAAAAT TAGTTGGGCA TGGGGTATGT
3301 ACCTGTGGTC CCAGCTACTC AGGGAGGCTG AGGTGGGAGG ATCACTTGAG
3351 CCCTTGAGCC TCAACTTGAG GAAGTTGAGG CTGCAGTGAG CCAAGATCAG
3401 TGCCACTGCA CTCCAGCCTG GGGCGACAGA GCAAGACTCT CTCCAAAAAA
3451 AAAAAAAAGT CTTAAAAATA GCTGTTTTTG TTTTCCATGT TTGTTTCATA
3501 AATTTTTTTT TTTTTTTTTT TTTTGAGATA GAGTCTCGCT CTATGGCCCA
3551 GGCTGGAGTG CAGTGGCTCA ATCTTGGCTC ACTGCAAACT CTACCTCCTG
3601 GGTCCAAGTG ATTCTCCCGC CTCAGCCTTC CGAGTAGCAG GAATTACAAA
3651 CGTGCGCCAC CACACCTGGC TAATTTTTAT ATTTTTAATA GAGATGGGGT
3701 TTGACTATGT TGGCCAGGCT GGTCTTGAAC TCCTGACTTA GTGATCCGCC
3751 TGCCTTGGCC TCCCAAAGTG CTGGGATTAC AGGCGTGAGC CACTGCGTCC
3801 GGCCTAATTT TAAAAGTTTA AAATGGATAA TTTTTATTGG CTGTGTGTTT
3851 CATGATTACC AGACTATGTT TCTCTCTCTT GTAGAGGTCC TTTGTTCTCC
3901 AATGTTGCTG TCAACATTCA GTCATTTCTC CTTATTTCAC ATGGCAGCAA
3951 ATATGTATGT TTTGTGGAGC TTCTCTTCCA GCATAGTGAA CATTCTGGGT
4001 CAAGAGCAGT TCATGGCAGT GTACCTATCT GCAGGTAATA TGCTTTAATC
4051 TCGGGGCCTT TGAGAGTATA AGCACTCTAA GCTATCTGCA GAACGGACAA
4101 AGGGAATGAT TACTGCCATA TTCTACACGT AGTGAGTGCT CAGAACATAT
4151 TTGTTTCTCA CAGTGTATGT AGAGAAGGGA GCCACAGATT GGTGGAGATG
4201 TTGCCTTTTC TGTTCATTTT GCTGATTTCT TCTTACATAT GAATTATGTG
4251 GGTATGTTTA ATTTTAAGTT AGGATAAACA GGCGTTAAGT AAGGGTTAGT
4301 GTAGAATTTA AGCATGTCAT TTTTGTAATC TCATCGGGCC TTGATTTCAT
4351 TAGTTTAGGC CCTCCATTTT ATAGATAGTG GTTCCCAGAC TTCCCGGCTG
4401 CCTCAATCTC CTGGGTCTTT GTTAAATAAC CTTAAGCAAG CTCATTTCCC
4451 CCAGTGTGTT CAGTTCACAG AAAGCTTTAA ATCAGAGCTA TACAATATGA
4501 TTGTCAAGAG TGAGTTTGTT CTGTCTTCTT TGCAAGAATG TAGCAGGGAA
4551 CCACTTCCTA GCCATGGTCT TGAAGATGGT ATCGTTTCTT ATTTCAGTTA

FIGURE 3B

```
4601 GGAAATTCTC ATGCATGAAT CCAGGTCCCT AGATGCTGCT AACGTGACAG
4651 TTGGTCAAAT TTTACTTACC TCTCTGTTTG TAAAATGTAC TTACTTAATA
4701 CAATATAAAA ATTAATTTCT AAAATCTCTA CATTTAGAAA CAGTATATCT
4751 GGCAGTTGTG CTGTGATGTA GTGAAAAACA CTAAGCTTGG CGATAGACCC
4801 AGGTTCAGAT CCTATTTCTA CTACCAGCTG AGTGATGTTG CAAAAATGAC
4851 TAAACCTCAT GATACTTACC TCCTCATGAC AAGGGGTTAA AGAAAGGACT
4901 ACATAAAAGC ATCTACCACA AGCCCCAGAG TAGATGCTTA ATTAGTGTTC
4951 ATCGAATACT TATGTGTATC TAGTCCTTCA AAAAAAGAAG CTGAGCATTG
5001 TGTTTGGCTT GTAAGATAAG TGTATAGTTC TTTCCCAAGC ACTAGTTATG
5051 TTGTAGTTAC AGAGGGTCTG TTTCAGATAC ATTAATTCCT GCTCCATAGG
5101 AGGTTTTTAA AAATGAGCCA CGTTGACTCA AATGGCACTG AAGCCAAAGA
5151 GACTTACGGG ATCATCCAGT CTGTTGTCCC ACCCCAGATA TTCTGATTTC
5201 GTGTGTCTGG AGTACAGCCA GAGAATATAC TCTTGGGAAT GAGTCTTCAT
5251 GTTATAGTTG AGGAAAATGG TAACTGAGAA GTGGAGTGAA TGACCGTGTC
5301 GCTCAGCAGA TCATGCAGCA GGTCAGACTT TTCATCCCCT GTAAAGTCGC
5351 TGAAATGATA GGCAGGAGAA GTATTCATGC CCGTACCCTC ACAGTGATCC
5401 AGATTGAAAC CCGACACTGT TTATCTGTGT AGAAATCAGA AATGAAAACC
5451 ATTTTCATGG CTGGATGTGG TGCCGCACGC CTGTAATCCC AGCTACTCAG
5501 GAGGCTGGGG GACAAGAATA ACTTGAACCC GGTAGGCAGA GGTTGCAGTG
5551 AGCCAAAATT GTACCACTGC ACTTCAGCAG CCGGGGCGAA AGAGTGAAAC
5601 TCTGTCTCAA AAAAAAAAAA AAAGAAAAGA AAAAAAAAAG TAAACCATTT
5651 TTATACCTCA CTTAAATTAT TGTAATGTGA CTTGTTTTTC AGGTGTTATT
5701 TCCAATTTTG TCAGTTACGT GGGTAAAGTT GCCACAGGAA GATATGGACC
5751 ATCACTTGGT GCAGTAAGTA TTTCTATTGT AAATTTTTTT TAATTTAATT
5801 TTTAAATTTA CTTTGAAATA AGTTTAGACT TAGAAGAATG TTGTAAAATT
5851 GATAAGTAGG TTCTCATATA CCCTTCACCC TACTGTTAAC TAACATCGAA
5901 ACCAAGAAAT TAACATTGAA ACAATACAGT TGACTAATTT AGAATTTATA
5951 CATTTGTAAA GCTTTGTAAA TGTCCGGCTA TAGCTTTTAA CCATTGGTCA
6001 TATATATATG TTTACCAGAG CAGAGTATAT CTCAGAACAG TAAGTGTGCA
6051 ATCCTCGTAA ACCAGAGAGC CTAATCCAGT ATTGGAAGAT TCTAATTATA
6101 GATTTGAATC TGGTACTTTA TCCTCCTATT TAGTCAATAT TGGAGTGCCT
6151 ACTAGGTGCT ATGCTAGAGC CTGGGGATAA CAGCTGGTGA GCAAGATGAT
6201 CACGATTATT TGTGTTGGTT TTAGAAAGTG GGGAACAACA ACAACAAAAA
6251 AGGCTCCTGC CCTCAGAGCT CTTATATTCT GGATGCTTAA AAAAATTTTT
6301 CTTAGGCTGG ATGCAGTGGT TTACACCTGT AATCCCAGCA CTTTGGGAGG
6351 CCAAGGTGAG AGGATGAGCC CAAGAATTCG AAACCAGCCC TGGTAACATA
6401 CCAAGATCCT ATCTGTACAA AAAAATTTAA AAAATTAACT GGGGGTGGTG
6451 GCTTATGCCG GTAGTCTCAG CTACTCAGGA GGCTGAGGAA GGAGGATAGC
6501 TTGAGCCTAG GAGGTTGAGG CTGCGGTGAG CTGTGATTGT ACCACTGCAC
6551 CCCAGCCTGG GTGACATAGC AAGACCCTAT CTCAAAAAAA AAATTTTTTT
6601 TTAAGTGTGT TTTGAGGCTG GGTGCAGTGG CTCACACCTG TAATCCCAGC
6651 ACTTTGGGAG GCTGAGGTGG GCAGCTCACT TGAGGTCAGG AGTTCAAGAC
6701 CAGCCTGGTC AACATGGTGA AACCCTGTCC CTCCTGAAAA TACAATAATT
6751 AGCCAGGTGT GGTTGTGCAT GCTTGTAATC CCAGCTACTC GGGAGGCTGA
6801 GGCAGGAGAA TTACTTGAAC CCAGCGGGTA GAGGTTGCAG TGAGCTGAGA
6851 TTGCACCACT GCACTCCAGC CTGGGTGACA GAACAAGACC CTGTCTCACA
```

FIGURE 3C

```
6901 GAACAAGACC CTGTCTCAAA GAAAAAAAAT TTTTTTAAGT GTCTTTTGAG
6951 TTTAATGGCA GATTTCTGGG CACATGGAAA TCTTTATGTA ATATTTCCTT
7001 ACACATTCAG TTTGTACTTA TTTAAATACT AATTCATTTA AATGCATTCA
7051 AATAGGGAAT TTCCTATTTA AAGGAACTCT AAAAAGGTCA ATTTTGAAAA
7101 GAATTCTTAT GTAAAATAAC CATTCCCTAA TTTGTATGTT CCCCAAATTT
7151 GTTTACACTT AATTTTCCTA GTGAGGCCTG TGTTCTGTCC TGTGACCACA
7201 TGCTTTCTTA AGCCTCCTTT TTTCCCTTCG TGGAATGTTT ATTTTCTTTA
7251 TACAATTTCG CTCTGATATA ATTTATATAT TTCGAATCAT ATTGTCTACC
7301 TCATTCAACA GCTAAGCACC TAATATATGA AGGCAGTGAA GACCACTAGG
7351 ATGAATCAGA GACTCAGAAT TCGAATTTAG CTGGGGAGAA AACATGCACA
7401 CATCTAATAC ACACTGAAAG GAATGAGGAT TCTCTAGAGG ACTTTGGGGG
7451 CTCTAAGAGT GAAGAGACCT TTCTAATTAG CTGAAAGGAC CTGCGAGGGC
7501 ATTTTGATGT GCTCTTGGAC AGCTGTTGTC CTCATCTTAT AGATAAGAAA
7551 CTGAAGTGCA AACTTAATGA AGTATGGCAG TAAGGTATTT GGAGTTAGAG
7601 TGGGGGTGAA TCCTGGTTCT GCTACTTACG TGTGATTTCT AGGACATATT
7651 ACTGAACTTC TCTGAATTTC AGTTTCCCTT TATAAAATGG GGATAACACC
7701 ATCTATTTCT GAGGTGCAAA GCAAGTACAT TTAGAGTGCT TAGCACAATA
7751 AGAAGCACAT GGTAAGAAAT GTGGACATGG TAGTTCCTGT TCAGTCATCA
7801 AAATCCTACA GCGCCGTGGT AGGATAACAT TATCCCCAAA TATCTTAATG
7851 AATCTGTGAT TAAAATTCAA GGAAATTAAA TCACCAGGTA TAATGGCATT
7901 TTTAATGAGA AATCTGGGAA AAAAACACCA TTAACAAAGT TGTGTTGTTA
7951 CAAAATGTAA AGCGTTAGTC CTCTTGGTTT AGTGAGACGT TATAAGATGC
8001 AGGGGACAGC CAGGCACAGT GGCTCACGCC TGTAGGCCCA ACACTTTGGG
8051 AGCCACGGCA GGAAGATCAC TTGAGCCCAG GAGGTTTGAG ACTAGCCTGG
8101 GCAACAAAGT GAGACCCCAT CTCTACAAAA AATTTCAAAA TTAAGCCGGG
8151 CATGGTGGCA TGCACCTGTA ATCCTACCTA CTCAGGAGAG GTGGGAGGGT
8201 GGGAGGAATG CCTGAGCCTA GGAGGGTGAG GCTGCTGTGA GCCATGAGCA
8251 TGCCACTGTG CTCCAACCTG GACAACATAG CGAGACCCCA TCTCAAAAAA
8301 AAAAAAAGAA AGTTGAATGG GACTGTTAAA ATATGTTTGT AAATTACTGT
8351 ATTGGTACTA TCCTGGATAA TTTTTAAACT TTTCTGTAGA GACAGGGTCT
8401 CCCTATGTTG CCAAGGCTGG TCTCAAACTC CTGGGCTCAA GTGATCCTCC
8451 TACCTGGGCC TCCCAAAGTG TTGGGATTAC TGGTGTGAGC CACTACACCC
8501 GGCCAATTGT CTTTTCTTAT TCAAGTTGAG ATTTTTCTGG TTCTTGATAT
8551 GATGAGTGAT TTTTCAGTTG AAGCCTGATC ATTTTAGATA TGATGAGACT
8601 TTGGATCTTA TTGAAATCTG CTGTTTCAGT GGTCTTCCTC TGACACTGTT
8651 CTGATGAGGA GAGGGGGTGC CGTGACTCGT TACTGCTGGG TGTAGGAGTA
8701 GACGTCCAGG TTCCTCACTC AGCCGCCTTT GCCTCCTGAG TGATAGGGGC
8751 TCTTGTCACT GCAGGGCAGG GATGGGAGCT GAGGGCGTGC AGGCTACCTA
8801 GTGTGCCTCT GCTAATGTCG CTGTGGCTAG GAGGAGCAAG GGTGCTTCTT
8851 TCCGCTGACA CCGCCTGTTA GGCGTATTGG GATGCCTCAT TACAGTGTGG
8901 CAAGGGTGGG AGTCTAGGCT CTGCTCAGCC TTTGCTGGGC ACCCGTTTCT
8951 CTAAATATTG TCTAAAAGGT CTCTTTTGCT AGGCTATCTT TTTTTGGTCC
9001 TTGACTAGAG AGAACATGTT GAGGGATGAT CGATATGAGG CCAAAAGAAA
9051 GCCCAGGGAA CTCACCACCA CAACATTGAT TGAATCTCAG GCTTCCTAGC
9101 TGGTCCGCTT TCCTCTCTCT TCCTTTCACA GTCCTCTTAC ATTTGTTTCA
9151 TATGTAACAC CCAGGGTCTT TAGCTGTACT TAGCTTTTGT AAGCAGAGGG
```

FIGURE 3D

```
9201 AGCAGATTCA CTTAAATTAT AATACCAAAT AAAGTTAAAA AACATAAGTA
9251 TGATAGATTT GAAGATTATA TAGATACAGA AAAATGTTTG TGAGCCCAGG
9301 CGCAGTGGCT CACAACTGTA ATCCCAGCAC TTTGGGAGGC CGAGGTGGGT
9351 GGATCACTTG AGGCCAGGAG TTCGAAACCA GCCTGGCCAA CATGGTGGAA
9401 CCCCATCTCT ACTAAAAATA CAAAAATTAG CTGGGCATGG TGGTGTGTAC
9451 CTGTTAGTCC CAGCTACTTG GCAGGCTGAG GTGTGAGAAT TAACTTGAAC
9501 CTGGGAGGCG GAGGTTGCAG TGAGATCGTG CCACCGCACT CCAGTTTGGG
9551 CAATAGCGAG ACTCTGTCTC AAAAAATATA TGTTTATGAA ATAAGTAAAA
9601 AAAAATCAGA TGTGCATATT GATTACAGGT ATATAACCAG TACATAAAAA
9651 TATTGATGGA GAACAAAAGA CCTTCACCTC TTCCCATGGA CCCACACCTC
9701 TTAGGTCTGT TGGATCAGGG TTCATGACTC ACTGTACTTA AACTGTGTAT
9751 GAATGTGAGC GTTTTCTGAG AAGAGAAGGG TTCATTTTCA TTAAATTCTT
9801 CTTTCTGACT CGAAAAAGTG AAAAAAGTCT CTCTGCATGG GAGTAAGCCC
9851 AAATATTTGT CAAAAAACAA GTTGTGATTT ATTCAGACAT ATAAATATTT
9901 AAATTTATAT AAAAGCCACA TCGAGAAAAT TCTAGAAGGA TGATGGAACT
9951 GTGTATGTAA TAATTACAAT AAGTTATAAT CACAAAAAAA CCAGCGTTCC
10001 ATGGAATTGT ACAGATAACG ACAATTTTTT TTAACAGATG GAGAATAATC
10051 ATCTATGGAA TAGTAGTTTA GAAGAACTTC ATAGAATTTT TTTTTTTTTT
10101 TTTTTTTTTT TTTTTTGGAG AGGGAGTTTC GTTCTTGTTG CCCAGGCTGG
10151 AGTGCAAAGG TGCGATCTCG GCTCGCTACA ACCTCTGCCT CCCGGGTTCA
10201 AGCGATTCTC CTGCCTCAAC CTCCTGAGTA GCTGGGATTA CAGGCATGCA
10251 CCACCATGCC CAGCTAATTT TGTATTTTTA GCAGAGACTG GGTTTCTTCA
10301 TGTTGGTCAG GCTGGTCTCG AACTCCAGAC CTCAGGTGAT CTGCCCGCCT
10351 CAGCCTCCCA AAGTCCTGGG ATTACAGGTG TAAGCGACTG TGCCTGGCAG
10401 AACTTCATAG AATTTTAATG CTCTTTTATA TCAACTAATC AAATTATATT
10451 TGCTTCATTT TGGGGAAACG TGTAATTTTG ATTTGTTTTG GGGTTTTTTT
10501 GAGATAAAGT GTCACTCTGT CGCCCAGGCT GGAGTACAGT GGCTCAATCT
10551 TGGCTCACCA CAACCTCAGC CTTCCGAGTA GCTGGGACTA CAGGCGCCCA
10601 CCACCACGTC TGGCTAATTT TTGTGTTTTT AGTAGAGACG GGGTTTCACT
10651 ATGTTGGCTA GGCTGGTCTT GAACTCCTGA CCTCAGGTGA TCCACCTGCC
10701 TCGGCCCCTC AGAGTGCTGG GATTACAGGC GTGAGCCACC GTGCCCGGCT
10751 ACAATTATAG TCTCTTGCAC AGAAGCCAGC TTGGTCAAAA TTCAGGTCTT
10801 CTTGGGTCCT CCTTTTGAGG AGTGTTCATG CTGTCCTTCC ATCTTGCAGT
10851 TACCCTGACT TCTAAGAATG CAACCCGAGC TTGTTTCCCT GTTGAGGCCA
10901 CTTGGCAGTT ATATGAGGGA CTGGGGACAT CTGAGATCTC TGGGACTCAT
10951 AATAATTTTC TTTAAAGTTT TAGTAATTCC CCAAATGTAA GATAATCTTG
11001 TATTCTGAAG CAACCCGTCA CATAGAAGAC ATTAAGAAAA CATTGATTAA
11051 GAGAGGTAGA TGCTATTTTC CAGAAACAAC CGTTTTTATA TGAAAAGGTA
11101 GGAACCTTTC TTTTTAATGA TAGGGGCTTC TTTCAAAAGT TATTTTGCTC
11151 TTAGGTGTCT TTTTTTTTTT TTTAAACATC TCATTCATAA ATAATTAAAA
11201 ACTTATGGGA AAGTTGCAGG GAATAGTACA GAGGACTCCC ATAAAGTCTT
11251 TTTTGTTTGT TTGTTTTGTT TTGTTTTGAG ACAGAGTCTC GCTGTTTTAC
11301 CCAGGCTGGA GTGCAGTGGG ACAATCTCGG CTCACTGCAA CCTCTGCCTC
11351 CCGGGTTCAA GCAATTCTCG GGCCTTAGCA TCCTAAGTAG GTGGGATTAT
11401 AAGCATCCGC CACCACGCCC AGCTAATTTT TTTTTTTTTT TTTTTTTTTG
11451 TATTTTTAGT AGAGACGGGG TTTTACCACG TTGGTCAGGC TGGTCTCAAA
```

FIGURE 3E

11501 CTCCTGACCT CAGGTGATCC ACCTGCCTCG GCCTCCAAAA GTGCTGGGAT
11551 TATAGGCGAG AGCCACTGCA CCCAGCCCCA TGTAGTCTTT TTAAAAAGCA
11601 GGCAACTCAG GTTTACTAGT TAACATGCAA AAAACTGCAC ATATTTAAAG
11651 TTTGGTAAGC TTTGACATGT AGACACCCGT GAAACCATCA CCACACTCAA
11701 GATCATGGAC ATATTCATCC CAAAAGCTTC CTAGTGGTCA CTCCTTCCTG
11751 CCCCTCCTCT ACCCCTGGCG ACAACTTACC TACTTCTACT AAAGATAAAT
11801 TAGTTTGCAA ATGGAACCAT ACAGCATATA CTAGTATTTG TTGTCCTGGC
11851 CTCATTTACT CTGTATAATT ACTTTGAGAC TCATCCATGT TCTGTGTATC
11901 AGTTTATTCC TTTATTATTT TTGAGACAGG GTCTTACTCT GTTGCCCAGG
11951 CAGGAGTGCA GTGGTGCAAT CATAGCTCAC TGTAACCTTG ACCTCCTGGG
12001 CTTAAGGGAT CCTCATGCCT CACAATGTGC TGGAATTACA GGCGTGAGCC
12051 ACCACACTGG CAATGTTTTG TTTCTTTATG AAGATGAATA AAGATTTCAC
12101 ATGAATTTTT TAAGATGAAA CATGCTTCAT GCATGCAGGT TTCTTTGGGC
12151 GTATTCATGC CCACTCCCTC TGGTTGGAGC TTTGTCAGAG AAGTGTGAGC
12201 AGTTCTTTCC TAGGCCATAG GTGAAAGATG CGCATGACAC GCTTAGCACT
12251 GTCCTTGCGG TTCATGAGGC ACATACATCT TACTGCCCCG TAGTAAAAAT
12301 TCAGTCTTTC CAAGCGATTA CTGTGTGAAG GACATTTAGT TCCTTCACCT
12351 ATTATTGGGG ACATAAGTAA CTGAAAGCTT TGAAGCTTTG TGCTCACCTA
12401 GAAATGTGCA GCATGTAAAC TTTCTAGAAA ATGTGCTGCT CTTTAGACCT
12451 TGTAGCCACT AAGCAGTTGC ATATTGAGTT TCCCATTCTC CCTGCTGTGT
12501 TACTTTGCAG TCTGGTGCCA TCATGACAGT CCTCGCAGCT GTCTGCACTA
12551 AGATCCCAGA AGGGAGGCTT GCCATTATTT TCCTTCCGAT GTTCACGTTC
12601 ACAGCAGGGA ATGTAAGTAT TTTTATGAAG TGCAGTGCTG GGGATAGTGG
12651 TGATGTTTTT ATGTTGAGTG GGTTCTTGCC CTTAAGTTAG AAATGTCAGT
12701 GCTGGAGCAA TCACAGTTGT GCCGCTTGTT TCTTGCTGCC TTTCAGGCCC
12751 TGAAAGCCAT TATCGCCATG GATACAGCAG GAATGATCCT GGGATGGAAA
12801 TTTTTTGATC ATGCGGCACA TCTTGGGGGA GCTCTTTTTG GAATGTAAGT
12851 TTGAGTGTAA TTGATTGCTA AACTGCTTCC TTGGGTCATG CGCTCCTCCT
12901 ACCCCAGCCT CACCCCTACC CCCCATCCCC ATGGCAGAGA CATTGAACTA
12951 TGCAACGGAA GCAGAAGCAG GTGGGCTTGG GAGGGTGAGG AAACCTCAAC
13001 ATGGCTTGCT TTGGGTTTAC CCAGCATACC TGGCTCATTG TAGAGACAGT
13051 CTGTGCCTTT ACCCTACGCT TAACCTTAAG TTGCCCCAAC TGTTGGCCTG
13101 TTATTCCCAG CCCCCTCTTA GAAGACTGCA GCCTGGCCCC CAGTCTATGC
13151 TGACATCTTC TTTTTCCCCT TCAGACTTTC CTGCCCTCCT CTCCCCTGCC
13201 TGGCGTCCCA CCCTGCTACC CTGACCTCTG TCTCGCCAGT GCTATTTAGA
13251 CATGCTGAGT TGGCGGAGCC ATTGCTCTGT ATGACTGGAG TAGAGGCCGG
13301 TGACTGCAAA CCAATGTGGA CCACTTACTG AGTACCCGCT GTATGCAGGC
13351 ACCAAGCTAG TTCCCTTATG TTATACTATT ACTACTCCCA TTTTACTGAT
13401 GGGAAACTGA GGCTCAGACA TCATCTTCCC CAGGCCAAAC AGCTCTTCAA
13451 TAGCAGAGCA GAGCTGTAAA CCCACCTCTA TAAGCCCTTT CCACCCCCAC
13501 CACACCATAT GGAATTGGTT GCTAAACTGC TTCCTTGGGT CACAGCAAAT
13551 GGCATTGTGG TTACAAGACC TTCCACGTGT GCTTCAAACA ATGGGGTTTT
13601 GCCTAGACTA GTGCTTAGTA GTAACTGTAT CACGGAAACA CGGTCAGGAC
13651 TCTTGGCGTC CATCTGATCG TGGGAGACCC GTCAGCATGA GCTGGATCCC
13701 CTCGGGGCCT GTCTTTTCTT ACATAAATGT TGCCTTTTGC CCTTACTTGG
13751 TTTTTATTTT GTTCCGCGAC AATGGAAAAC TTAATTTTTT TTTTTATTAA

FIGURE 3F

13801 AAAGAAAAAT CTATTCTGGC CAGGTGCAGT GGCTCACGCC TGTAATCCCA
13851 GCACTTTGGG AGGCCAAGGC AGGCGGATCA CAAGGTCAGG AGATCGAGAC
13901 CATCCTGGCT AACACAGTGA AACCCCGTCT CTACTAAAAA TACAAAAAAC
13951 TTAGCCGGGC GTGGTGGCGG GCGCCTGTAG TCCCAGCTAC TCGGGAGGCT
14001 GAGGCAGGAG AATGGTGTGA ACCCAGAAGG CAGAGCTTGC AGTGAGCCGA
14051 GATCACGCCA CTGCACTCCA GCCTGGGCGA CAAAGTGAGA CTCTGTCTCA
14101 AAAAAAAAAA AAAGAAAAAT CTATTCTAAG TGAAGCAGTT TTTCCCAGTA
14151 GGTGGCAGAA CTAAATGCCA TTATGCCATT TATAATTTTA AGTGATTAAA
14201 GAGGAGTAGT ATGTAGTATA TGCAAGGTCT AGCTCTAACA GCAGTGCAGT
14251 ATAAATAGTA GAAACTGACC TGATATTACA GTATGAGAAA CATGAAGGGG
14301 TTCTGTTTTG TGAGCTCTAA ATTTATCTTC CATGTATACT TCAAGGCTCT
14351 TCTCCCCAGT AGATTTTTAT TCATCTGAAC TATAATTAGG TGGCCTTTTT
14401 CCATTCTGAA AATAATTGGA TCAAATGCAT TTTAAAGTCC AGGGTCTGAA
14451 AGGTGGAGGA ATCCTTTCTC TTTACTGTTT CTAATTTAAA CTCCTTTTCA
14501 TTTACTAGAT TTCAGTCATG TCCAGAATTC ATCTTTTCTA AAAGCTTTAA
14551 TCTAGATTTA GAAATCTAAA ATCTTTTATT TATTTTTTTT TCGTTGAAGT
14601 GCCCTGATTT TGTTGGTGGT AAAGACTCCA TTAGTATCCA CTTATACATT
14651 TCCCTGACTT TGCCTCTGAC CAAACCTTAC AGTATTCACA TTGTACTGTT
14701 GCAATAATAA TAGCTAACAT ATTAATACAC TGAATATTTG CTGTGTGCCT
14751 AAGCTAAGGA TTTAATTCTC TTAAAATCCT GTGAGGTATT TTATTTTACA
14801 GAAAAAGAAA CTGCTTAAAG AAAGTAACTT ATCCAGGTCA CACAAGTAAC
14851 AATTGCAGAG CTGGAGTTTC AGATGAGGGC TGGCTTGCGC TGCCGCTACA
14901 GAAAAGAGTG CCCTAGAAAT CGGTCATCTT GCATTTCCCG ATTTTAGTTT
14951 AGCCAAATGA AAAATTCCTT TTGGATTTAT GAGTATAATC AGACAGTATA
15001 CCTGTGAAAT TAAAGTATTT GACTCTTTGC TTGAAATAAG TAGGTTAAAA
15051 AGATTTGGGT GGCCGGGCGC AGTGGCTCAC GCCTGTAATC CCAGCACTTT
15101 GGGAGGCTGA GGCAAGTAGA TCATTTGAGG TCAGGAGTTC GAGACCAGCC
15151 TGACCAATAT GGGGAAACCT CGTCTCTACT AAAAATACAA AAATTAGCCG
15201 GGCGTGGTGG TGCATGCCTG TAATACCAGC TACTTGGAGG CTGAGGCAGG
15251 AGAATCACTT GAAGCCAGGA GGCAGAGGTT ACAGTGAGCT GAGATCACGC
15301 CACTGCACTC CAGCCTGGGC AACAGAGCGC GACTCTGTCT AACAACAAAA
15351 AAGATTTGGG AAAACACTTT ATTAATGAAG AGTTCCTGAC AAAGTGATTT
15401 TTTTGGGGAG AATTTTTATA ATTGCATTTG AATATTAGGG TGCTCCTTTT
15451 TCTCTCATTC TAAATTCACC AGAGACTTAA GCACAGAGAA TTTTTATTAC
15501 ATGCCTGTTA ATTAATGTGT ATAATCAGAT TTTAACTATA TTTAGTGAAT
15551 ATTAAGATTC AGGTACAAAT CAAGCCCTTT ATAATTAAAC ATACACATTC
15601 AGAACATTTT TAAAATATTA AAACATTAAA CTGCTCTTCT CACCCACTCC
15651 AAGTCAAATA GCATTTTTTC AGTCAGGTGT CTGGGAGCTC GATGCAAGAT
15701 AACAAAATCT GGTCTCTGCC TCAGGGAACA TGAAATCTGT TTGGGGAAGC
15751 CAGAGCAAAA ATAAAGGTTT TAATAGCAAG CTCTCACTAA CTGCCCCTGG
15801 AAATCCACCC CACATCCTCC AGGAAGCCTT TCTCTACCCC CAGTGCCCTC
15851 AGGAGCTTCT CCAAGGCAGG CCCTTCCCAG AGCGCAGTGT GCTCCCCAGC
15901 TCACAGGAGA TGCTCCCTAC ACGCTGCAGG AAAGTCCAGT GCCTGCAGCA
15951 CAGGCTTCAG CAGCAGACTC GGGTTCTAGT CTCAGTCTGC TGATTCCTAG
16001 TTGTGGAACC TGAGCAGGCG AAGTTACTAA ACCTCTCTGT GCGTCAGCCT
16051 CCCAGGCTCG TTGCTTCAGG CCGCAGTTAG GCTGTGTGAA CAGGAGAGTG

FIGURE 3G

16101 GGGATGGGAA CTAGGTATCT TAAAGCGGGG CAGAGTTTGG ATGAGCGGGC
16151 CACCCTTCGT ATAGTTAGGA GGAAGATGAC GGGAGGCATG GAAGCTGGGA
16201 TAGCCATCCT GAGTCAGTGC TAATTCTGAC ACTTCAGAAC ATCGAGTCAG
16251 TCTGACCTGC GAGTGAGCTT TCATTGACCA CTTAGAAACT ATTAGCACCT
16301 TGGACAAACT ACTTTCTTTC AGACCTGGTT GCTTCATGTC TGCGATGGGA
16351 AAACTGATAC TTAACTTGCA GATAGTGGTG AATCAAAAGT AGTATATGTG
16401 AAGTACTCAC ACACTGCGGA GCATTCAGCC ATCGTCCCAT CCTACTTCTA
16451 CCTTTTACAT ATTGTAATAT GAAAGCTAAA CCATTTCTCG ATGTGAGTCA
16501 GTTTTAATCG GCTACATAGT GAGTGGCATT CGATTTTAAA AATGTCAACT
16551 TGGGATCTGT CACCATGCTA CTTACCATTT GTATGTCACA CTGTTTGAAT
16601 GTCGGACCTG GTTTGTTTTT CTCCAGATGG TATGTTACTT ACGGTCATGA
16651 ACTGATTTGG AAGAACAGGG AGCCGCTAGT GAAAATCTGG CATGAAATAA
16701 GGACTAATGG CCCCAAAAAA GGAGGTGGCT CTAAGTAAAA CTGGGATTGG
16751 ACAGTAGTGG TGCATCTGGT CCTTGCCGCC TGAGAGCCCC AGGAGACATC
16801 GGCTAGAGTG ACCATGGCTA TGCTCCCGTC TGGAAGATGC CAGCATCTGG
16851 CCTCCCACTG TTTTCAGCTG TGTCCCCCAG TCCGTGTCTT TTTAGAATGT
16901 GAATGATGAT AAAGTTGTGA AATAAAGGTT TCTATCTAGT TTGTAAGCAG
16951 ATGTGTGTGT TCTCTCTTTA AGGGGCCGAC ACGGCTCTGG CATTTTGCTT
17001 TGGTTGTTGC ATTGACAGGA CCTGGGGAGA GTGCACCCTG AAAGGCCTGA
17051 TCAGAACATG AAGGCGCTGG TTGCCTGTCT TTGGACCCTC CAGTGCCTCT
17101 GCTTAGCCTT CACTCTTCCT TGCCTCCCCC TCCCCTGGGT TGGCTGCACA
17151 TAAAAGTCAA GAGTATCCCC TCTCCAGCAC AATCTGAAAT AACAGCTGCA
17201 GTATTTTCTC AATTTTCAGG AAAGGTAGTG TTTTCTGGCA GTGAGTGGCA
17251 TATACAAAAA GCTATTTTCA GGTTTTGCTT TCTAGGTTCA ATTTGTAGAT
17301 AAATTAAGAG GTAGAAAGAA GTGATTTGGG TAAATTCAGA CTTGAAATCT
17351 GAGCCGAATT TTATCTTCTG TTTGAAAGTG TTCTAATTGA AGCGTCTCAC
17401 TGAAAATAGC AGATAGTGGC TGTCGTCGTC ACAGCCCTCA CTGTTGTGGA
17451 ATTCATGTTA CCCTCGTGAC TGAGAATGAC ATCTAGGAAA TGCAGTTTGA
17501 GAGTATGTTC TTCTTGAAGT CATTTACAGG AGAATTTTTA GTCTTTTGAT
17551 GGCTTCAAAA TGTTATACCA AGTCTTGCAG CTTTGTCCTG GGAGGATCGA
17601 AGGCCCTGAT TTCAGCCTCC TGTGGCCGAT CGGACTCAGG TTGTGTGCCG
17651 TGGGGGATGG GAATGGCGGC TTTGGAAAAG GAGTGGGAGT GGTGCCCACC
17701 TCACCAGGCA AGTGAGAACT GCATGGCAGC ACGCGCCCAG CACATAGAAA
17751 TTGTCCAGTA TTTGGCAGTC CTTCATATCC TTCTTCCATC AGGCTGGACT
17801 TGTTTCTACT ATGATTTACA GTTATTCTTC CCAGGCACAG GATTCTGTTC
17851 TAAACTCGTA TCACTTCTAG GGGAGAGAGT TATCTTAGCC ATCATTTTGC
17901 CAGCGAGGAA ACGGCACACG TGGTGTAGGG GCACTGCCCA AGGTCACAAT
17951 GCTTTGCTCT GACATCTGCT AACAACTGCA ACACAGATGA GGCAAGATGC
18001 GTTTTCCAGA GATGGGATAG GAGGCTGAGT TCATAGGGAC ATTCCCTCTA
18051 GAGCCCAACA TTAATTCACA TCGTGCTTTG GGCAGACCAG GCAAAGAGGC
18101 AATGAAGACA TCTCTGTGTC CCTGCTTTGT GACTGGGAAA AAGTTAGAAG
18151 TCCCTGTAGC ATCTCCTGGT CCCTAAAACC CCTCAATGCT GGAGCCTCTG
18201 TGCATGGCCT GGGGAGGCCA GAACCTGGCT GTGGCCGGAG AAGCCTTGCT
18251 GTCCACAGCT CCCTCCTGAT TGCCCACGAG GGTGCTTCAC TTTCTCCTCT
18301 TGGCTTCTCT GGGGACCCGC GATCACTGCC TTCAAGGCCA TGCACTCCCT
18351 GGCCCGTGGG CCTCTTGGGC TGTGCCGCCT CCACTGGCAT CTGAAGTGTG

FIGURE 3H

```
18401 GGGTACCTAG GAACATGCCG TGGCTGCCGT CTCCCTCATT CCATACACTT
18451 CTTGAGTGGG TGCACTTGCT GAAGCCTCAG TTATCTGTGA GGATTCTGAG
18501 CTCCAGACCC ACAGAATCTC TCTGTACTCT TAGTAAATGT GTCTACTGCA
18551 ACACACGCAT GGTTCCAGGC TCTGGGACCA CCCCCCCGCC CTGCACAGGC
18601 CCCTCAAATA GCACTCGGCT TAAGGAGTGA CACGAGCAAT CGGTGAAGTC
18651 TGAAACCCGG AGCCATTCGA GATCTCCCTC TCTCGCCTCT TATTTCTAGA
18701 ATTCAGCCCC TCAGCCTTCC CAGTGCCTGT GACTCCGTGG TGGTCCTCAC
18751 TTCTTAGTCC CTGGACTGTT GAGCCTGTTC TTCCAGCTGG TCTCCAAAGC
18801 AACCCTGTGC TTCTCCATAT GCCTGCCAGA GTGCTAAAAA CACGTCTGTC
18851 ATTCCTTTGT TGTCACCTGT GAAAAACTTT TATTTATTTG AGACAGGGTC
18901 TCTCTCTCTC TCTCTCGTCC AGGCTGGAGT TCAGTGGTGC AATCTAGATG
18951 GTCACTACAC TCAGGGAGTT GGGGATGGCT CAGAGCTGTT AACAGAGAGG
19001 GGACTGCCCA GGAGGACCTG CGTGAGGGGT GGGGGTGGGA TGACAAGGAA
19051 CCAGCTCTGG GAGTTGAAAG ACCTGGATTC AAGTCTCAAC CCAAGCCCTG
19101 GCCAGCTCTG GGACCCCGGA CAAGTCGGCC TCACTCTCTG CCCCTCAGTG
19151 GGCTCCTGTG TAGATGGGGA TAATGATGGC TTTATATCCT GAGAATGTGG
19201 GGAGGGGATT AAGTGGCCAA AATACCTGAG AGTGCGCACT CAGTGCCTGG
19251 CTCAGCAAAT GCCCTTGTTC CCTCCTTCCC TCTCCCCAGA ACCCCTCCTC
19301 CCCTTCTTCT TCTTTTTTTT TTTTTTTTTT TGACCCAGAG TCTTGCTATG
19351 TTGCCCAGGC TGGAGTGCAG TGGCACAATC TCGGCTCACT GCAACCTCCA
19401 CCTCCTGGCT TCAGGCAATT CTTGTGCCTC AGCCTCTCGA GTAGCTGGGA
19451 TTACAGGCAG GCACCATCAC GCCCGGCTAA TTTTTTTTTT TTTTTTTTGT
19501 AGTAGAAATG GGATTTCACC ATATTGGCAG GATGTTCTCG ATCTCCTGAC
19551 CTCAGGTGAT CCACTCGCCT TGGCCTCCCA AAGTGCTGGG ATTATAGGTG
19601 TCAGCCACTG CGCCCAGCCC CCATTGTTTA TCTCCTCTTC CATTTCTTGT
19651 GGGGACTTTT AAAGGAAAAA TCAGGTTGGT GGGCTGGGGG AGGGCATAGC
19701 TGAGACCACC TTGAGGGCAC CAAGCTCACT GACCAC  (SEQ ID NO:3)
```

FEATURES:

| | |
|---|---|
| Start: | 2002 |
| Exon: | 2002-2098 |
| Intron: | 2099-5692 |
| Exon: | 5693-5763 |
| Intron: | 5764-12510 |
| Exon: | 12511-12612 |
| Intron: | 12613-12746 |
| Exon: | 12747-12844 |
| Intron: | 12845-16626 |
| Exon: | 16627-16735 |
| Stop: | 16736 |

SNPs:

| DNA Position | Major | Minor | Domain | Protein Position | Major | Minor |
|---|---|---|---|---|---|---|

FIGURE 3I

| | | | |
|---|---|---|---|
| 237 | T | C | Beyond ORF(5') |
| 783 | G | T | Beyond ORF(5') |
| 1187 | C | T | Beyond ORF(5') |
| 1227 | - | A T | Beyond ORF(5') |
| 1450 | T | C G | Beyond ORF(5') |
| 3925 | C | T | Intron |
| 5539 | G | C | Intron |
| 7220 | T | C | Intron |
| 7396 | G | A | Intron |
| 9048 | A | C | Intron |
| 9952 | T | C | Intron |
| 10197 | G | A T | Intron |
| 10245 | C | G | Intron |
| 10427 | C | T | Intron |
| 10583 | T | C | Intron |
| 10651 | A | G | Intron |
| 11125 | G | A | Intron |
| 12025 | A | C | Intron |
| 12391 | T | G | Intron |
| 13001 | A | G | Intron |
| 13147 | A | G | Intron |
| 13587 | A | G | Intron |
| 13681 | T | G | Intron |
| 14336 | A | G | Intron |
| 14729 | A | G | Intron |
| 15124 | C | T | Intron |
| 15907 | A | G | Intron |
| 16341 | - | G T | Intron |
| 16786 | G | C | Beyond ORF(3') |
| 17159 | G | A | Beyond ORF(3') |
| 17976 | - | T C | Beyond ORF(3') |
| 18001 | G | A | Beyond ORF(3') |
| 18021 | G | T | Beyond ORF(3') |
| 18022 | A | G | Beyond ORF(3') |
| 18042 | T | G | Beyond ORF(3') |
| 18375 | C | T | Beyond ORF(3') |
| 19244 | T | C | Beyond ORF(3') |

Context:
DNA
Position

237 CGAGGTTTCTTCATGTTGGTCAGGCTGGTCTCGAACTCCCGACCTCAGGTGATCCGTCCG
CCTCAGCCTCCCAAAGTACTGCTGGGATTACAGACGTGAGCCACCGCACCCGGCCTTTAT
CTTTCATTTTTTTTCATGTATTTTCCTTTATTTTAATCACTTTATCCAGAAACATATCCT

FIGURE 3J

CGTCTTGACAGTGCTGTGGTGCCTGTGGTTTCCAGAAGCTGGGTGTGCTGTGTGTC
[T,C]
GTGGTTTGAGGAAGTTGCCCATGGAACTGACAGAGGAAGCAGAGTAGTCGTTGCCATTTT
TCAGCCTAGTAGGCAGGATCAGGGACCCCATCTTGCTCTCTTTGCCTTGAACCACAATTA
GAATAAAACACCAAAGCCCTGACTGATCATGATCATAGCAATCCGATCTTTATGATCATG
GCCAGACCATTCTCAGGTCGTCTTTACCCTAAGATATCAATCACTGGGTATGACAACCTA
GACCTAAGGGTGCACTCTGGGTAGTAAAGATGATTAACTCTCCCAAAGGAATCTAAGGAA

783 AAGGGTGCACTCTGGGTAGTAAAGATGATTAACTCTCCCAAAGGAATCTAAGGAATCCAG
AGCAACACGAATCACTGCTCTCTTCCTATAGGGTAAACCTCCCAAGACTCCAGTCCCTGT
GAGGAGGCTCTGCCCGCCTGCCCTTCCCAGGGTTCCAGGCTCCACATTGGGAGGTGTACA
CAGTGCTCTTCGCTCTTCATTGCCTTGTGTATGATCCCTTTTCCCATCTTTGCATAAATG
CTGTCCCTCTCACCATCTTTAAAAGAGTTCTGGGTAATTATTTACCAAAGGTGGTATAAT
[G,T]
CTGTCACAGTCCCTGCTAGTGAGACATCTGATACAACTGATGGAATCAGTTCAACAAAAT
GCAGTAAAATTTTATTTAATGTACTACGGAGAAAGAAAAAATGCTACCAGTTATAAGATG
CATCCTGATTTCAGATATTAAAATGGAAAAAATGTCTTAAGATCTGTGAAAAATGTAGCT
TCCTTTCCCACCTCTCAAGTGGGAGAGCAAAAACTGGACAGACTAGAAATGCCAGGGGCT
AGCTGAGAACCTTACAGAATGAGCAACTGCGGAAGCCACAGGTAACACCGAGATGTAGAT

1187 CTACCAGTTATAAGATGCATCCTGATTTCAGATATTAAAATGGAAAAAATGTCTTAAGAT
CTGTGAAAAATGTAGCTTCCTTTCCCACCTCTCAAGTGGGAGAGCAAAAACTGGACAGAC
TAGAAATGCCAGGGGCTAGCTGAGAACCTTACAGAATGAGCAACTGCGGAAGCCACAGGT
AACACCGAGATGTAGATCAGCTGCCAGGGACAAGACAAAGAATGTTTTCTAAAGTAAATC
CTCTTACCAGTATGTTATTGAAATCAGTCCTTATTGGCATCGAAGAAGGTGAAAGTGCTA
[C,T]
TTGCCTGTTGCCTACAGAGACTGGAGGAATGACAAATGTTTAAATTATTTTAATTCAACA
AGTAGAGGAATACCTGCTATGTGAAGGAGTTGTGGCAATTCATAAAATTAATATATTTTT
TGAAGTTTGTAGTTTTCAATAATAATTTCTTATCTAAAATGTAACAAGTTAATTATATTA
TCGAATAAACCTCAATTTCGTAGTACTAACAACATCAACACTTACAGAAAAAGGAAAGTC
ACTCAACTCCCACATGTAAACAGACTTTAGAAGCAGTTGCAGAGGTTTTCTAAATTATCC

1227 TGGAAAAAATGTCTTAAGATCTGTGAAAAATGTAGCTTCCTTTCCCACCTCTCAAGTGGG
AGAGCAAAAACTGGACAGACTAGAAATGCCAGGGGCTAGCTGAGAACCTTACAGAATGAG
CAACTGCGGAAGCCACAGGTAACACCGAGATGTAGATCAGCTGCCAGGGACAAGACAAAG
AATGTTTTCTAAAGTAAATCCTCTTACCAGTATGTTATTGAAATCAGTCCTTATTGGCAT
CGAAGAAGGTGAAAGTGCTACTTGCCTGTTGCCTACAGAGACTGGAGGAATGACAAATGT
[-,A,T]
TAAATTATTTTAATTCAACAAGTAGAGGAATACCTGCTATGTGAAGGAGTTGTGGCAATT
CATAAAATTAATATATTTTTTGAAGTTTGTAGTTTTCAATAATAATTTCTTATCTAAAAT
GTAACAAGTTAATTATATTATCGAATAAACCTCAATTTCGTAGTACTAACAACATCAACA
CTTACAGAAAAAGGAAAGTCACTCAACTCCCACATGTAAACAGACTTTAGAAGCAGTTGC
AGAGGTTTTCTAAATTATCCCTGAATTCCTATCACATGACTATTTTTCTCAGACATGTTG

1450 TCAGTCCTTATTGGCATCGAAGAAGGTGAAAGTGCTACTTGCCTGTTGCCTACAGAGACT
GGAGGAATGACAAATGTTTAAATTATTTTAATTCAACAAGTAGAGGAATACCTGCTATGT

FIGURE 3K

GAAGGAGTTGTGGCAATTCATAAAATTAATATATTTTTTGAAGTTTGTAGTTTTCAATAA
TAATTTCTTATCTAAAATGTAACAAGTTAATTATATTATCGAATAAACCTCAATTTCGTA
GTACTAACAACATCAACACTTACAGAAAAAGGAAAGTCACTCAACTCCCACATGTAAACA
[T,C,G]
ACTTTAGAAGCAGTTGCAGAGGTTTTCTAAATTATCCCTGAATTCCTATCACATGACTAT
TTTTCTCAGACATGTTGACCTTCACCTACACAGATGACTCACATATGTTTCCATAAGCTG
GCAGTAAGTTTAAGAAGCATACCATGCCCTGAGGAAAAAGAAGTAATGTTAGCTCTTCTA
CTCTTGGCCAAAGAACCTAATTCTGTATATTACTTCTGTCTTTGGTTTGGCTATTATAGA
CAATAAATTATTGATCTGATTATAATTGAGAAAAGTAAGCTCTTCTAAAGAAGTAAAATA

3925 GCCTTCCGAGTAGCAGGAATTACAAACGTGCGCCACCACACCTGGCTAATTTTTATATTT
TTAATAGAGATGGGGTTTGACTATGTTGGCCAGGCTGGTCTTGAACTCCTGACTTAGTGA
TCCGCCTGCCTTGGCCTCCCAAAGTGCTGGGATTACAGGCGTGAGCCACTGCGTCCGGCC
TAATTTTAAAAGTTTAAAATGGATAATTTTTATTGGCTGTGTGTTTCATGATTACCAGAC
TATGTTTCTCTCTCTTGTAGAGGTCCTTTGTTCTCCAATGTTGCTGTCAACATTCAGTCA
[C,T]
TTCTCCTTATTTCACATGGCAGCAAATATGTATGTTTTGTGGAGCTTCTCTTCCAGCATA
GTGAACATTCTGGGTCAAGAGCAGTTCATGGCAGTGTACCTATCTGCAGGTAATATGCTT
TAATCTCGGGGCCTTTGAGAGTATAAGCACTCTAAGCTATCTGCAGAACGGACAAAGGGA
ATGATTACTGCCATATTCTACACGTAGTGAGTGCTCAGAACATATTTGTTTCTCACAGTG
TATGTAGAGAAGGGAGCCACAGATTGGTGGAGATGTTGCCTTTTCTGTTCATTTTGCTGA

5539 ATGAGTCTTCATGTTATAGTTGAGGAAAATGGTAACTGAGAAGTGGAGTGAATGACCGTG
TCGCTCAGCAGATCATGCAGCAGGTCAGACTTTTCATCCCCTGTAAAGTCGCTGAAATGA
TAGGCAGGAGAAGTATTCATGCCCGTACCCTCACAGTGATCCAGATTGAAACCCGACACT
GTTTATCTGTGTAGAAATCAGAAATGAAAACCATTTTCATGGCTGGATGTGGTGCCGCAC
GCCTGTAATCCCAGCTACTCAGGAGGCTGGGGGACAAGAATAACTTGAACCCGGTAGGCA
[G,C]
AGGTTGCAGTGAGCCAAAATTGTACCACTGCACTTCAGCAGCCGGGGCGAAAGAGTGAAA
CTCTGTCTCAAAAAAAAAAAAAAAGAAAAGAAAAAAAAAAGTAAACCATTTTTATACCTC
ACTTAAATTATTGTAATGTGACTTGTTTTTCAGGTGTTATTTCCAATTTTGTCAGTTACG
TGGGTAAAGTTGCCACAGGAAGATATGGACCATCACTTGGTGCAGTAAGTATTTCTATTG
TAAATTTTTTTTAATTTAATTTTTAAATTTACTTTGAAATAAGTTTAGACTTAGAAGAAT

7220 AGAAAAAAAATTTTTTTAAGTGTCTTTTGAGTTTAATGGCAGATTTCTGGGCACATGGAA
ATCTTTATGTAATATTTCCTTACACATTCAGTTTGTACTTATTTAAATACTAATTCATTT
AAATGCATTCAAATAGGGAATTTCCTATTTAAAGGAACTCTAAAAAGGTCAATTTTGAAA
AGAATTCTTATGTAAAATAACCATTCCCTAATTTGTATGTTCCCCAAATTTGTTTACACT
TAATTTTCCTAGTGAGGCCTGTGTTCTGTCCTGTGACCACATGCTTTCTTAAGCCTCCTT
[T,C]
TTTCCCTTCGTGGAATGTTTATTTTCTTTATACAATTTCGCTCTGATATAATTTATATAT
TTCGAATCATATTGTCTACCTCATTCAACAGCTAAGCACCTAATATATGAAGGCAGTGAA
GACCACTAGGATGAATCAGAGACTCAGAATTCGAATTTAGCTGGGGAGAAAACATGCACA
CATCTAATACACACTGAAAGGAATGAGGATTCTCTAGAGGACTTTGGGGGCTCTAAGAGT
GAAGAGACCTTTCTAATTAGCTGAAAGGACCTGCGAGGGCATTTTGATGTGCTCTTGGAC

FIGURE 3L

7396 GAAAAGAATTCTTATGTAAAATAACCATTCCCTAATTTGTATGTTCCCCAAATTTGTTTA
CACTTAATTTTCCTAGTGAGGCCTGTGTTCTGTCCTGTGACCACATGCTTTCTTAAGCCT
CCTTTTTTCCCTTCGTGGAATGTTTATTTTCTTTATACAATTTCGCTCTGATATAATTTA
TATATTTCGAATCATATTGTCTACCTCATTCAACAGCTAAGCACCTAATATATGAAGGCA
GTGAAGACCACTAGGATGAATCAGAGACTCAGAATTCGAATTTAGCTGGGGAGAAAACAT
[G,A]
CACACATCTAATACACACTGAAAGGAATGAGGATTCTCTAGAGGACTTTGGGGGCTCTAA
GAGTGAAGAGACCTTTCTAATTAGCTGAAAGGACCTGCGAGGGCATTTTGATGTGCTCTT
GGACAGCTGTTGTCCTCATCTTATAGATAAGAAACTGAAGTGCAAACTTAATGAAGTATG
GCAGTAAGGTATTTGGAGTTAGAGTGGGGGTGAATCCTGGTTCTGCTACTTACGTGTGAT
TTCTAGGACATATTACTGAACTTCTCTGAATTTCAGTTTCCCTTTATAAAATGGGGATAA

9048 GGCTCTTGTCACTGCAGGGCAGGGATGGGAGCTGAGGGCGTGCAGGCTACCTAGTGTGCC
TCTGCTAATGTCGCTGTGGCTAGGAGGAGCAAGGGTGCTTCTTTCCGCTGACACCGCCTG
TTAGGCGTATTGGGATGCCTCATTACAGTGTGGCAAGGGTGGGAGTCTAGGCTCTGCTCA
GCCTTTGCTGGGCACCCGTTTCTCTAAATATTGTCTAAAAGGTCTCTTTTGCTAGGCTAT
CTTTTTTTGGTCCTTGACTAGAGAGAACATGTTGAGGGATGATCGATATGAGGCCAAAAG
[A,C]
AAGCCCAGGGAACTCACCACCACAACATTGATTGAATCTCAGGCTTCCTAGCTGGTCCGC
TTTCCTCTCTCTTCCTTTCACAGTCCTCTTACATTTGTTTCATATGTAACACCCAGGGTC
TTTAGCTGTACTTAGCTTTTGTAAGCAGAGGGAGCAGATTCACTTAAATTATAATACCAA
ATAAAGTTAAAAAACATAAGTATGATAGATTTGAAGATTATATAGATACAGAAAAATGTT
TGTGAGCCCAGGCGCAGTGGCTCACAACTGTAATCCCAGCACTTTGGGAGGCCGAGGTGG

9952 ATTGATGGAGAACAAAAGACCTTCACCTCTTCCCATGGACCCACACCTCTTAGGTCTGTT
GGATCAGGGTTCATGACTCACTGTACTTAAACTGTGTATGAATGTGAGCGTTTTCTGAGA
AGAGAAGGGTTCATTTTCATTAAATTCTTCTTTCTGACTCGAAAAAGTGAAAAAAGTCTC
TCTGCATGGGAGTAAGCCCAAATATTTGTCAAAAAACAAGTTGTGATTTATTCAGACATA
TAAATATTTAAATTTATATAAAAGCCACATCGAGAAAATTCTAGAAGGATGATGGAACTG
[T,C]
GTATGTAATAATTACAATAAGTTATAATCACAAAAAAACCAGCGTTCCATGGAATTGTAC
AGATAACGACAATTTTTTTTAACAGATGGAGAATAATCATCTATGGAATAGTAGTTTAGA
AGAACTTCATAGAATTTTTTTTTTTTTTTTTTTTTTTTTTTTTTTTGGAGAGGGAGTTTCGT
TCTTGTTGCCCAGGCTGGAGTGCAAAGGTGCGATCTCGGCTCGCTACAACCTCTGCCTCC
CGGGTTCAAGCGATTCTCCTGCCTCAACCTCCTGAGTAGCTGGGATTACAGGCATGCACC

10197 ATTTAAATTTATATAAAAGCCACATCGAGAAAATTCTAGAAGGATGATGGAACTGTGTAT
GTAATAATTACAATAAGTTATAATCACAAAAAAACCAGCGTTCCATGGAATTGTACAGAT
AACGACAATTTTTTTTAACAGATGGAGAATAATCATCTATGGAATAGTAGTTTAGAAGAA
CTTCATAGAATTTTTTTTTTTTTTTTTTTTTTTTTTTTTTTTGGAGAGGGAGTTTCGTTCTT
GTTGCCCAGGCTGGAGTGCAAAGGTGCGATCTCGGCTCGCTACAACCTCTGCCTCCCGGG
[G,A,T]
TCAAGCGATTCTCCTGCCTCAACCTCCTGAGTAGCTGGGATTACAGGCATGCACCACCAT
GCCCAGCTAATTTTGTATTTTTAGCAGAGACTGGGTTTCTTCATGTTGGTCAGGCTGGTC
TCGAACTCCAGACCTCAGGTGATCTGCCCGCCTCAGCCTCCCAAAGTCCTGGGATTACAG
GTGTAAGCGACTGTGCCTGGCAGAACTTCATAGAATTTTAATGCTCTTTTATATCAACTA

FIGURE 3M

ATCAAATTATATTTGCTTCATTTTGGGGAAACGTGTAATTTTGATTTGTTTTGGGGTTTT

10245 GGAACTGTGTATGTAATAATTACAATAAGTTATAATCACAAAAAAACCAGCGTTCCATGG
AATTGTACAGATAACGACAATTTTTTTTAACAGATGGAGAATAATCATCTATGGAATAGT
AGTTTAGAAGAACTTCATAGAATTTTTTTTTTTTTTTTTTTTTTTTTTTTTTGGAGAGGG
AGTTTCGTTCTTGTTGCCCAGGCTGGAGTGCAAAGGTGCGATCTCGGCTCGCTACAACCT
CTGCCTCCCGGGTTCAAGCGATTCTCCTGCCTCAACCTCCTGAGTAGCTGGGATTACAGG
[C,G]
ATGCACCACCATGCCCAGCTAATTTTGTATTTTTAGCAGAGACTGGGTTTCTTCATGTTG
GTCAGGCTGGTCTCGAACTCCAGACCTCAGGTGATCTGCCCGCCTCAGCCTCCCAAAGTC
CTGGGATTACAGGTGTAAGCGACTGTGCCTGGCAGAACTTCATAGAATTTTAATGCTCTT
TTATATCAACTAATCAAATTATATTTGCTTCATTTTGGGGAAACGTGTAATTTTGATTTG
TTTTGGGGTTTTTTTGAGATAAAGTGTCACTCTGTCGCCCAGGCTGGAGTACAGTGGCTC

10427 TTTCGTTCTTGTTGCCCAGGCTGGAGTGCAAAGGTGCGATCTCGGCTCGCTACAACCTCT
GCCTCCCGGGTTCAAGCGATTCTCCTGCCTCAACCTCCTGAGTAGCTGGGATTACAGGCA
TGCACCACCATGCCCAGCTAATTTTGTATTTTTAGCAGAGACTGGGTTTCTTCATGTTGG
TCAGGCTGGTCTCGAACTCCAGACCTCAGGTGATCTGCCCGCCTCAGCCTCCCAAAGTCC
TGGGATTACAGGTGTAAGCGACTGTGCCTGGCAGAACTTCATAGAATTTTAATGCTCTTT
[C,T]
ATATCAACTAATCAAATTATATTTGCTTCATTTTGGGGAAACGTGTAATTTTGATTTGTT
TTGGGGTTTTTTTGAGATAAAGTGTCACTCTGTCGCCCAGGCTGGAGTACAGTGGCTCAA
TCTTGGCTCACCACAACCTCAGCCTTCCGAGTAGCTGGGACTACAGGCGCCCACCACCAC
GTCTGGCTAATTTTTGTGTTTTTAGTAGAGACGGGGTTTCACTATGTTGGCTAGGCTGGT
CTTGAACTCCTGACCTCAGGTGATCCACCTGCCTCGGCCCCTCAGAGTGCTGGGATTACA

10583 AGAGACTGGGTTTCTTCATGTTGGTCAGGCTGGTCTCGAACTCCAGACCTCAGGTGATCT
GCCCGCCTCAGCCTCCCAAAGTCCTGGGATTACAGGTGTAAGCGACTGTGCCTGGCAGAA
CTTCATAGAATTTTAATGCTCTTTTATATCAACTAATCAAATTATATTTGCTTCATTTTG
GGGAAACGTGTAATTTTGATTTGTTTTGGGGTTTTTTTGAGATAAAGTGTCACTCTGTCG
CCCAGGCTGGAGTACAGTGGCTCAATCTTGGCTCACCACAACCTCAGCCTTCCGAGTAGC
[T,C]
GGGACTACAGGCGCCCACCACCACGTCTGGCTAATTTTTGTGTTTTTAGTAGAGACGGGG
TTTCACTATGTTGGCTAGGCTGGTCTTGAACTCCTGACCTCAGGTGATCCACCTGCCTCG
GCCCCTCAGAGTGCTGGGATTACAGGCGTGAGCCACCGTGCCCGGCTACAATTATAGTCT
CTTGCACAGAAGCCAGCTTGGTCAAAATTCAGGTCTTCTTGGGTCCTCCTTTTGAGGAGT
GTTCATGCTGTCCTTCCATCTTGCAGTTACCCTGACTTCTAAGAATGCAACCCGAGCTTG

10651 CAGCCTCCCAAAGTCCTGGGATTACAGGTGTAAGCGACTGTGCCTGGCAGAACTTCATAG
AATTTTAATGCTCTTTTATATCAACTAATCAAATTATATTTGCTTCATTTTGGGGAAACG
TGTAATTTTGATTTGTTTTGGGGTTTTTTTGAGATAAAGTGTCACTCTGTCGCCCAGGCT
GGAGTACAGTGGCTCAATCTTGGCTCACCACAACCTCAGCCTTCCGAGTAGCTGGGACTA
CAGGCGCCCACCACCACGTCTGGCTAATTTTTGTGTTTTTAGTAGAGACGGGGTTTCACT
[A,G]
TGTTGGCTAGGCTGGTCTTGAACTCCTGACCTCAGGTGATCCACCTGCCTCGGCCCCTCA
GAGTGCTGGGATTACAGGCGTGAGCCACCGTGCCCGGCTACAATTATAGTCTCTTGCACA

FIGURE 3N

GAAGCCAGCTTGGTCAAAATTCAGGTCTTCTTGGGTCCTCCTTTTGAGGAGTGTTCATGC
TGTCCTTCCATCTTGCAGTTACCCTGACTTCTAAGAATGCAACCCGAGCTTGTTTCCCTG
TTGAGGCCACTTGGCAGTTATATGAGGGACTGGGGACATCTGAGATCTCTGGGACTCATA

11125 TTCATGCTGTCCTTCCATCTTGCAGTTACCCTGACTTCTAAGAATGCAACCCGAGCTTGT
TTCCCTGTTGAGGCCACTTGGCAGTTATATGAGGGACTGGGGACATCTGAGATCTCTGGG
ACTCATAATAATTTTCTTTAAAGTTTTAGTAATTCCCCAAATGTAAGATAATCTTGTATT
CTGAAGCAACCCGTCACATAGAAGACATTAAGAAAACATTGATTAAGAGAGGTAGATGCT
ATTTTCCAGAAACAACCGTTTTTATATGAAAAGGTAGGAACCTTTCTTTTTAATGATAGG
[G,A]
GCTTCTTTCAAAAGTTATTTTGCTCTTAGGTGTCTTTTTTTTTTTTTTAAACATCTCATT
CATAAATAATTAAAAACTTATGGGAAAGTTGCAGGGAATAGTACAGAGGACTCCCATAAA
GTCTTTTTTGTTTGTTTGTTTTGTTTTGTTTTGAGACAGAGTCTCGCTGTTTTACCCAGG
CTGGAGTGCAGTGGGACAATCTCGGCTCACTGCAACCTCTGCCTCCCGGGTTCAAGCAAT
TCTCGGGCCTTAGCATCCTAAGTAGGTGGGATTATAAGCATCCGCCACCACGCCCAGCTA

12025 AGCTTCCTAGTGGTCACTCCTTCCTGCCCCTCCTCTACCCCTGGCGACAACTTACCTACT
TCTACTAAAGATAAATTAGTTTGCAAATGGAACCATACAGCATATACTAGTATTTGTTGT
CCTGGCCTCATTTACTCTGTATAATTACTTTGAGACTCATCCATGTTCTGTGTATCAGTT
TATTCCTTTATTATTTTTGAGACAGGGTCTTACTCTGTTGCCCAGGCAGGAGTGCAGTGG
TGCAATCATAGCTCACTGTAACCTTGACCTCCTGGGCTTAAGGGATCCTCATGCCTCACA
[A,C]
TGTGCTGGAATTACAGGCGTGAGCCACCACACTGGCAATGTTTTGTTTCTTTATGAAGAT
GAATAAAGATTTCACATGAATTTTTTAAGATGAAACATGCTTCATGCATGCAGGTTTCTT
TGGGCGTATTCATGCCCACTCCCTCTGGTTGGAGCTTTGTCAGAGAAGTGTGAGCAGTTC
TTTCCTAGGCCATAGGTGAAAGATGCGCATGACACGCTTAGCACTGTCCTTGCGGTTCAT
GAGGCACATACATCTTACTGCCCCGTAGTAAAAATTCAGTCTTTCCAAGCGATTACTGTG

12391 AAGATTTCACATGAATTTTTTAAGATGAAACATGCTTCATGCATGCAGGTTTCTTTGGGC
GTATTCATGCCCACTCCCTCTGGTTGGAGCTTTGTCAGAGAAGTGTGAGCAGTTCTTTCC
TAGGCCATAGGTGAAAGATGCGCATGACACGCTTAGCACTGTCCTTGCGGTTCATGAGGC
ACATACATCTTACTGCCCCGTAGTAAAAATTCAGTCTTTCCAAGCGATTACTGTGTGAAG
GACATTTAGTTCCTTCACCTATTATTGGGGACATAAGTAACTGAAAGCTTTGAAGCTTTG
[T,G]
GCTCACCTAGAAATGTGCAGCATGTAAACTTTCTAGAAAATGTGCTGCTCTTTAGACCTT
GTAGCCACTAAGCAGTTGCATATTGAGTTTCCCATTCTCCCTGCTGTGTTACTTTGCAGT
CTGGTGCCATCATGACAGTCCTCGCAGCTGTCTGCACTAAGATCCCAGAAGGGAGGCTTG
CCATTATTTTCCTTCCGATGTTCACGTTCACAGCAGGGAATGTAAGTATTTTTATGAAGT
GCAGTGCTGGGGATAGTGGTGATGTTTTTATGTTGAGTGGGTTCTTGCCCTTAAGTTAGA

13001 GCTGGAGCAATCACAGTTGTGCCGCTTGTTTCTTGCTGCCTTTCAGGCCCTGAAAGCCAT
TATCGCCATGGATACAGCAGGAATGATCCTGGATGGAAATTTTTTGATCATGCGGCACA
TCTTGGGGGAGCTCTTTTTGGAATGTAAGTTTGAGTGTAATTGATTGCTAAACTGCTTCC
TTGGGTCATGCGCTCCTCCTACCCCAGCCTCACCCCTACCCCCCATCCCCATGGCAGAGA
CATTGAACTATGCAACGGAAGCAGAAGCAGGTGGGCTTGGGAGGGTGAGGAAACCTCAAC
[A,G]

FIGURE 3O

TGGCTTGCTTTGGGTTTACCCAGCATACCTGGCTCATTGTAGAGACAGTCTGTGCCTTTA
CCCTACGCTTAACCTTAAGTTGCCCCAACTGTTGGCCTGTTATTCCCAGCCCCCTCTTAG
AAGACTGCAGCCTGGCCCCCAGTCTATGCTGACATCTTCTTTTTCCCCTTCAGACTTTCC
TGCCCTCCTCTCCCCTGCCTGGCGTCCCACCCTGCTACCCTGACCTCTGTCTCGCCAGTG
CTATTTAGACATGCTGAGTTGGCGGAGCCATTGCTCTGTATGACTGGAGTAGAGGCCGGT

13147 AAGTTTGAGTGTAATTGATTGCTAAACTGCTTCCTTGGGTCATGCGCTCCTCCTACCCCA
GCCTCACCCCTACCCCCCATCCCCATGGCAGAGACATTGAACTATGCAACGGAAGCAGAA
GCAGGTGGGCTTGGGAGGGTGAGGAAACCTCAACATGGCTTGCTTTGGGTTTACCCAGCA
TACCTGGCTCATTGTAGAGACAGTCTGTGCCTTTACCCTACGCTTAACCTTAAGTTGCCC
CAACTGTTGGCCTGTTATTCCCAGCCCCCTCTTAGAAGACTGCAGCCTGGCCCCCAGTCT
[A,G]
TGCTGACATCTTCTTTTTCCCCTTCAGACTTTCCTGCCCTCCTCTCCCCTGCCTGGCGTC
CCACCCTGCTACCCTGACCTCTGTCTCGCCAGTGCTATTTAGACATGCTGAGTTGGCGGA
GCCATTGCTCTGTATGACTGGAGTAGAGGCCGGTGACTGCAAACCAATGTGGACCACTTA
CTGAGTACCCGCTGTATGCAGGCACCAAGCTAGTTCCCTTATGTTATACTATTACTACTC
CCATTTTACTGATGGGAAACTGAGGCTCAGACATCATCTTCCCCAGGCCAAACAGCTCTT

13587 GGAGTAGAGGCCGGTGACTGCAAACCAATGTGGACCACTTACTGAGTACCCGCTGTATGC
AGGCACCAAGCTAGTTCCCTTATGTTATACTATTACTACTCCCATTTTACTGATGGGAAA
CTGAGGCTCAGACATCATCTTCCCCAGGCCAAACAGCTCTTCAATAGCAGAGCAGAGCTG
TAAACCCACCTCTATAAGCCCTTTCCACCCCCACCACACCATATGGAATTGGTTGCTAAA
CTGCTTCCTTGGGTCACAGCAAATGGCATTGTGGTTACAAGACCTTCCACGTGTGCTTCA
[A,G]
ACAATGGGGTTTTGCCTAGACTAGTGCTTAGTAGTAACTGTATCACGGAAACACGGTCAG
GACTCTTGGCGTCCATCTGATCGTGGGAGACCCGTCAGCATGAGCTGGATCCCCTCGGGG
CCTGTCTTTTCTTACATAAATGTTGCCTTTTGCCCTTACTTGGTTTTTATTTTGTTCCGC
GACAATGGAAAACTTAATTTTTTTTTTTTATTAAAAAGAAAAATCTATTCTGGCCAGGTGC
AGTGGCTCACGCCTGTAATCCCAGCACTTTGGGAGGCCAAGGCAGGCGGATCACAAGGTC

13681 ACTACTCCCATTTTACTGATGGGAAACTGAGGCTCAGACATCATCTTCCCCAGGCCAAAC
AGCTCTTCAATAGCAGAGCAGAGCTGTAAACCCACCTCTATAAGCCCTTTCCACCCCCAC
CACACCATATGGAATTGGTTGCTAAACTGCTTCCTTGGGTCACAGCAAATGGCATTGTGG
TTACAAGACCTTCCACGTGTGCTTCAAACAATGGGGTTTTGCCTAGACTAGTGCTTAGTA
GTAACTGTATCACGGAAACACGGTCAGGACTCTTGGCGTCCATCTGATCGTGGGAGACCC
[T,G]
TCAGCATGAGCTGGATCCCCTCGGGGCCTGTCTTTTCTTACATAAATGTTGCCTTTTGCC
CTTACTTGGTTTTTATTTTGTTCCGCGACAATGGAAAACTTAATTTTTTTTTTTTATTAAA
AAGAAAAATCTATTCTGGCCAGGTGCAGTGGCTCACGCCTGTAATCCCAGCACTTTGGGA
GGCCAAGGCAGGCGGATCACAAGGTCAGGAGATCGAGACCATCCTGGCTAACACAGTGAA
ACCCCGTCTCTACTAAAAATACAAAAAACTTAGCCGGGCGTGGTGGCGGGCGCCTGTAGT

14336 CTTGCAGTGAGCCGAGATCACGCCACTGCACTCCAGCCTGGGCGACAAAGTGAGACTCTG
TCTCAAAAAAAAAAAAAAGAAAAATCTATTCTAAGTGAAGCAGTTTTTCCCAGTAGGTGG
CAGAACTAAATGCCATTATGCCATTTATAATTTTAAGTGATTAAAGAGGAGTAGTATGTA
GTATATGCAAGGTCTAGCTCTAACAGCAGTGCAGTATAAATAGTAGAAACTGACCTGATA

FIGURE 3P

TTACAGTATGAGAAACATGAAGGGGTTCTGTTTTGTGAGCTCTAAATTTATCTTCCATGT
[A,G]
TACTTCAAGGCTCTTCTCCCCAGTAGATTTTTATTCATCTGAACTATAATTAGGTGGCCT
TTTTCCATTCTGAAAATAATTGGATCAAATGCATTTTAAAGTCCAGGGTCTGAAAGGTGG
AGGAATCCTTTCTCTTTACTGTTTCTAATTTAAACTCCTTTTCATTTACTAGATTTCAGT
CATGTCCAGAATTCATCTTTTCTAAAAGCTTTAATCTAGATTTAGAAATCTAAAATCTTT
TATTTATTTTTTTTTCGTTGAAGTGCCCTGATTTTGTTGGTGGTAAAGACTCCATTAGTA

14729

ATTTTAAAGTCCAGGGTCTGAAAGGTGGAGGAATCCTTTCTCTTTACTGTTTCTAATTTA
AACTCCTTTTCATTTACTAGATTTCAGTCATGTCCAGAATTCATCTTTTCTAAAAGCTTT
AATCTAGATTTAGAAATCTAAAATCTTTTATTTATTTTTTTTTCGTTGAAGTGCCCTGAT
TTTGTTGGTGGTAAAGACTCCATTAGTATCCACTTATACATTTCCCTGACTTTGCCTCTG
ACCAAACCTTACAGTATTCACATTGTACTGTTGCAATAATAATAGCTAACATATTAATAC
[A,G]
CTGAATATTTGCTGTGTGCCTAAGCTAAGGATTTAATTCTCTTAAAATCCTGTGAGGTAT
TTTATTTTACAGAAAAAGAAACTGCTTAAAGAAAGTAACTTATCCAGGTCACACAAGTAA
CAATTGCAGAGCTGGAGTTTCAGATGAGGGCTGGCTTGCGCTGCCGCTACAGAAAAGAGT
GCCCTAGAAATCGGTCATCTTGCATTTCCCGATTTTAGTTTAGCCAAATGAAAAATTCCT
TTTGGATTTATGAGTATAATCAGACAGTATACCTGTGAAATTAAAGTATTTGACTCTTTG

15124

GTAACTTATCCAGGTCACACAAGTAACAATTGCAGAGCTGGAGTTTCAGATGAGGGCTGG
CTTGCGCTGCCGCTACAGAAAAGAGTGCCCTAGAAATCGGTCATCTTGCATTTCCCGATT
TTAGTTTAGCCAAATGAAAAATTCCTTTTGGATTTATGAGTATAATCAGACAGTATACCT
GTGAAATTAAAGTATTTGACTCTTTGCTTGAAATAAGTAGGTTAAAAAGATTTGGGTGGC
CGGGCGCAGTGGCTCACGCCTGTAATCCCAGCACTTTGGGAGGCTGAGGCAAGTAGATCA
[C,T]
TTGAGGTCAGGAGTTCGAGACCAGCCTGACCAATATGGGGAAACCTCGTCTCTACTAAAA
ATACAAAAATTAGCCGGGCGTGGTGGTGCATGCCTGTAATACCAGCTACTTGGAGGCTGA
GGCAGGAGAATCACTTGAAGCCAGGAGGCAGAGGTTACAGTGAGCTGAGATCACGCCACT
GCACTCCAGCCTGGGCAACAGAGCGCGACTCTGTCTAACAACAAAAAAGATTTGGGAAAA
CACTTTATTAATGAAGAGTTCCTGACAAAGTGATTTTTTTGGGGAGAATTTTTATAATTG

15907

TTTTTAAAATATTAAAACATTAAACTGCTCTTCTCACCCACTCCAAGTCAAATAGCATTT
TTTCAGTCAGGTGTCTGGGAGCTCGATGCAAGATAACAAAATCTGGTCTCTGCCTCAGGG
AACATGAAATCTGTTTGGGGAAGCCAGAGCAAAAATAAAGGTTTTAATAGCAAGCTCTCA
CTAACTGCCCCTGGAAATCCACCCCACATCCTCCAGGAAGCCTTTCTCTACCCCCAGTGC
CCTCAGGAGCTTCTCCAAGGCAGGCCCTTCCCAGAGCGCAGTGTGCTCCCCAGCTCACAG
[A,G]
AGATGCTCCCTACACGCTGCAGGAAAGTCCAGTGCCTGCAGCACAGGCTTCAGCAGCAGA
CTCGGGTTCTAGTCTCAGTCTGCTGATTCCTAGTTGTGGAACCTGAGCAGGCGAAGTTAC
TAAACCTCTCTGTGCGTCAGCCTCCCAGGCTCGTTGCTTCAGGCCGCAGTTAGGCTGTGT
GAACAGGAGAGTGGGGATGGAACTAGGTATCTTAAAGCGGGGCAGAGTTTGGATGAGCG
GGCCACCCTTCGTATAGTTAGGAGGAAGATGACGGGAGGCATGGAAGCTGGGATAGCCAT

16341

GCGTCAGCCTCCCAGGCTCGTTGCTTCAGGCCGCAGTTAGGCTGTGTGAACAGGAGAGTG
GGGATGGGAACTAGGTATCTTAAAGCGGGGCAGAGTTTGGATGAGCGGGCCACCCTTCGT

FIGURE 3Q

ATAGTTAGGAGGAAGATGACGGGAGGCATGGAAGCTGGGATAGCCATCCTGAGTCAGTGC
TAATTCTGACACTTCAGAACATCGAGTCAGTCTGACCTGCGAGTGAGCTTTCATTGACCA
CTTAGAAACTATTAGCACCTTGGACAAACTACTTTCTTTCAGACCTGGTTGCTTCATGTC
[-,G,T]
GCGATGGGAAAACTGATACTTAACTTGCAGATAGTGGTGAATCAAAAGTAGTATATGTGA
AGTACTCACACACTGCGGAGCATTCAGCCATCGTCCCATCCTACTTCTACCTTTTACATA
TTGTAATATGAAAGCTAAACCATTTCTCGATGTGAGTCAGTTTTAATCGGCTACATAGTG
AGTGGCATTCGATTTTAAAAATGTCAACTTGGGATCTGTCACCATGCTACTTACCATTTG
TATGTCACACTGTTTGAATGTCGGACCTGGTTTGTTTTTCTCCAGATGGTATGTTACTTA

16786 TCTCGATGTGAGTCAGTTTTAATCGGCTACATAGTGAGTGGCATTCGATTTTAAAAATGT
CAACTTGGGATCTGTCACCATGCTACTTACCATTTGTATGTCACACTGTTTGAATGTCGG
ACCTGGTTTGTTTTTCTCCAGATGGTATGTTACTTACGGTCATGAACTGATTTGGAAGAA
CAGGGAGCCGCTAGTGAAAATCTGGCATGAAATAAGGACTAATGGCCCCAAAAAAGGAGG
TGGCTCTAAGTAAAACTGGGATTGGACAGTAGTGGTGCATCTGGTCCTTGCCGCCTGAGA
[G,C]
CCCCAGGAGACATCGGCTAGAGTGACCATGGCTATGCTCCCGTCTGGAAGATGCCAGCAT
CTGGCCTCCCACTGTTTTCAGCTGTGTCCCCCAGTCCGTGTCTTTTTAGAATGTGAATGA
TGATAAAGTTGTGAAATAAAGGTTTCTATCTAGTTTGTAAGCAGATGTGTGTGTTCTCTC
TTTAAGGGGCCGACACGGCTCTGGCATTTTGCTTTGGTTGTTGCATTGACAGGACCTGGG
GAGAGTGCACCCTGAAAGGCCTGATCAGAACATGAAGGCGCTGGTTGCCTGTCTTTGGAC

17159 TGTTTTCAGCTGTGTCCCCCAGTCCGTGTCTTTTTAGAATGTGAATGATGATAAAGTTGT
GAAATAAAGGTTTCTATCTAGTTTGTAAGCAGATGTGTGTGTTCTCTCTTTAAGGGGCCG
ACACGGCTCTGGCATTTTGCTTTGGTTGTTGCATTGACAGGACCTGGGGAGAGTGCACCC
TGAAAGGCCTGATCAGAACATGAAGGCGCTGGTTGCCTGTCTTTGGACCCTCCAGTGCCT
CTGCTTAGCCTTCACTCTTCCTTGCCTCCCCCTCCCCTGGGTTGGCTGCACATAAAAGTC
[G,A]
AGAGTATCCCCTCTCCAGCACAATCTGAAATAACAGCTGCAGTATTTTCTCAATTTTCAG
GAAAGGTAGTGTTTTCTGGCAGTGAGTGGCATATACAAAAAGCTATTTTCAGGTTTTGCT
TTCTAGGTTCAATTTGTAGATAAATTAAGAGGTAGAAAGAAGTGATTTGGGTAAATTCAG
ACTTGAAATCTGAGCCGAATTTTATCTTCTGTTTGAAAGTGTTCTAATTGAAGCGTCTCA
CTGAAAATAGCAGATAGTGGCTGTCGTCGTCACAGCCCTCACTGTTGTGGAATTCATGTT

17976 AAAAGGAGTGGGAGTGGTGCCCACCTCACCAGGCAAGTGAGAACTGCATGGCAGCACGCG
CCCAGCACATAGAAATTGTCCAGTATTTGGCAGTCCTTCATATCCTTCTTCCATCAGGCT
GGACTTGTTTCTACTATGATTTACAGTTATTCTTCCCAGGCACAGGATTCTGTTCTAAAC
TCGTATCACTTCTAGGGGAGAGAGTTATCTTAGCCATCATTTTGCCAGCGAGGAAACGGC
ACACGTGGTGTAGGGGCACTGCCCAAGGTCACAATGCTTTGCTCTGACATCTGCTAACAA
[-,T,C]
TGCAACACAGATGAGGCAAGATGCGTTTTCCAGAGATGGGATAGGAGGCTGAGTTCATAG
GGACATTCCCTCTAGAGCCCAACATTAATTCACATCGTGCTTTGGGCAGACCAGGCAAAG
AGGCAATGAAGACATCTCTGTGTCCCTGCTTTGTGACTGGGAAAAAGTTAGAAGTCCCTG
TAGCATCTCCTGGTCCCTAAAACCCCTCAATGCTGGAGCCTCTGTGCATGGCCTGGGGAG
GCCAGAACCTGGCTGTGGCCGGAGAAGCCTTGCTGTCCACAGCTCCCTCCTGATTGCCCA

FIGURE 3R

18001 TCACCAGGCAAGTGAGAACTGCATGGCAGCACGCGCCCAGCACATAGAAATTGTCCAGTA
TTTGGCAGTCCTTCATATCCTTCTTCCATCAGGCTGGACTTGTTTCTACTATGATTTACA
GTTATTCTTCCCAGGCACAGGATTCTGTTCTAAACTCGTATCACTTCTAGGGGAGAGAGT
TATCTTAGCCATCATTTTGCCAGCGAGGAAACGGCACACGTGGTGTAGGGGCACTGCCCA
AGGTCACAATGCTTTGCTCTGACATCTGCTAACAACTGCAACACAGATGAGGCAAGATGC
[G,A]
TTTTCCAGAGATGGGATAGGAGGCTGAGTTCATAGGGACATTCCCTCTAGAGCCCAACAT
TAATTCACATCGTGCTTTGGGCAGACCAGGCAAAGAGGCAATGAAGACATCTCTGTGTCC
CTGCTTTGTGACTGGGAAAAAGTTAGAAGTCCCTGTAGCATCTCCTGGTCCCTAAAACCC
CTCAATGCTGGAGCCTCTGTGCATGGCCTGGGGAGGCCAGAACCTGGCTGTGGCCGGAGA
AGCCTTGCTGTCCACAGCTCCCTCCTGATTGCCCACGAGGGTGCTTCACTTTCTCCTCTT

18021 GCATGGCAGCACGCGCCCAGCACATAGAAATTGTCCAGTATTTGGCAGTCCTTCATATCC
TTCTTCCATCAGGCTGGACTTGTTTCTACTATGATTTACAGTTATTCTTCCCAGGCACAG
GATTCTGTTCTAAACTCGTATCACTTCTAGGGGAGAGAGTTATCTTAGCCATCATTTTGC
CAGCGAGGAAACGGCACACGTGGTGTAGGGGCACTGCCCAAGGTCACAATGCTTTGCTCT
GACATCTGCTAACAACTGCAACACAGATGAGGCAAGATGCGTTTTCCAGAGATGGGATAG
[G,T]
AGGCTGAGTTCATAGGGACATTCCCTCTAGAGCCCAACATTAATTCACATCGTGCTTTGG
GCAGACCAGGCAAAGAGGCAATGAAGACATCTCTGTGTCCCTGCTTTGTGACTGGGAAAA
AGTTAGAAGTCCCTGTAGCATCTCCTGGTCCCTAAAACCCCTCAATGCTGGAGCCTCTGT
GCATGGCCTGGGGAGGCCAGAACCTGGCTGTGGCCGGAGAAGCCTTGCTGTCCACAGCTC
CCTCCTGATTGCCCACGAGGGTGCTTCACTTTCTCCTCTTGGCTTCTCTGGGGACCCGCG

18022 CATGGCAGCACGCGCCCAGCACATAGAAATTGTCCAGTATTTGGCAGTCCTTCATATCCT
TCTTCCATCAGGCTGGACTTGTTTCTACTATGATTTACAGTTATTCTTCCCAGGCACAGG
ATTCTGTTCTAAACTCGTATCACTTCTAGGGGAGAGAGTTATCTTAGCCATCATTTTGCC
AGCGAGGAAACGGCACACGTGGTGTAGGGGCACTGCCCAAGGTCACAATGCTTTGCTCTG
ACATCTGCTAACAACTGCAACACAGATGAGGCAAGATGCGTTTTCCAGAGATGGGATAGG
[A,G]
GGCTGAGTTCATAGGGACATTCCCTCTAGAGCCCAACATTAATTCACATCGTGCTTTGGG
CAGACCAGGCAAAGAGGCAATGAAGACATCTCTGTGTCCCTGCTTTGTGACTGGGAAAAA
GTTAGAAGTCCCTGTAGCATCTCCTGGTCCCTAAAACCCCTCAATGCTGGAGCCTCTGTG
CATGGCCTGGGGAGGCCAGAACCTGGCTGTGGCCGGAGAAGCCTTGCTGTCCACAGCTCC
CTCCTGATTGCCCACGAGGGTGCTTCACTTTCTCCTCTTGGCTTCTCTGGGGACCCGCGA

18042 ACATAGAAATTGTCCAGTATTTGGCAGTCCTTCATATCCTTCTTCCATCAGGCTGGACTT
GTTTCTACTATGATTTACAGTTATTCTTCCCAGGCACAGGATTCTGTTCTAAACTCGTAT
CACTTCTAGGGGAGAGAGTTATCTTAGCCATCATTTTGCCAGCGAGGAAACGGCACACGT
GGTGTAGGGGCACTGCCCAAGGTCACAATGCTTTGCTCTGACATCTGCTAACAACTGCAA
CACAGATGAGGCAAGATGCGTTTTCCAGAGATGGGATAGGAGGCTGAGTTCATAGGGACA
[T,G]
TCCCTCTAGAGCCCAACATTAATTCACATCGTGCTTTGGGCAGACCAGGCAAAGAGGCAA
TGAAGACATCTCTGTGTCCCTGCTTTGTGACTGGGAAAAAGTTAGAAGTCCCTGTAGCAT
CTCCTGGTCCCTAAAACCCCTCAATGCTGGAGCCTCTGTGCATGGCCTGGGGAGGCCAGA
ACCTGGCTGTGGCCGGAGAAGCCTTGCTGTCCACAGCTCCCTCCTGATTGCCCACGAGGG

FIGURE 3S

TGCTTCACTTTCTCCTCTTGGCTTCTCTGGGGACCCGCGATCACTGCCTTCAAGGCCATG

18375 GCTTTGGGCAGACCAGGCAAAGAGGCAATGAAGACATCTCTGTGTCCCTGCTTTGTGACT
GGGAAAAAGTTAGAAGTCCCTGTAGCATCTCCTGGTCCCTAAAACCCCTCAATGCTGGAG
CCTCTGTGCATGGCCTGGGGAGGCCAGAACCTGGCTGTGGCCGGAGAAGCCTTGCTGTCC
ACAGCTCCCTCCTGATTGCCCACGAGGGTGCTTCACTTTCTCCTCTTGGCTTCTCTGGGG
ACCCGCGATCACTGCCTTCAAGGCCATGCACTCCCTGGCCCGTGGGCCTCTTGGGCTGTG
[C,T]
CGCCTCCACTGGCATCTGAAGTGTGGGGTACCTAGGAACATGCCGTGGCTGCCGTCTCCC
TCATTCCATACACTTCTTGAGTGGGTGCACTTGCTGAAGCCTCAGTTATCTGTGAGGATT
CTGAGCTCCAGACCCACAGAATCTCTCTGTACTCTTAGTAAATGTGTCTACTGCAACACA
CGCATGGTTCCAGGCTCTGGGACCACCCCCCCGCCCTGCACAGGCCCCTCAAATAGCACT
CGGCTTAAGGAGTGACACGAGCAATCGGTGAAGTCTGAAACCCGGAGCCATTCGAGATCT

19244 CTAGATGGTCACTACACTCAGGGAGTTGGGGATGGCTCAGAGCTGTTAACAGAGAGGGGA
CTGCCCAGGAGGACCTGCGTGAGGGGTGGGGGTGGGATGACAAGGAACCAGCTCTGGGAG
TTGAAAGACCTGGATTCAAGTCTCAACCCAAGCCCTGGCCAGCTCTGGGACCCCGGACAA
GTCGGCCTCACTCTCTGCCCCTCAGTGGGCTCCTGTGTAGATGGGGATAATGATGGCTTT
ATATCCTGAGAATGTGGGGAGGGGATTAAGTGGCCAAAATACCTGAGAGTGCGCACTCAG
[T,C]
GCCTGGCTCAGCAAATGCCCTTGTTCCCTCCTTCCCTCTCCCCAGAACCCCTCCTCCCCT
TCTTCTTCTTTTTTTTTTTTTTTTTTTTGACCCAGAGTCTTGCTATGTTGCCCAGGCTGGA
GTGCAGTGGCACAATCTCGGCTCACTGCAACCTCCACCTCCTGGCTTCAGGCAATTCTTG
TGCCTCAGCCTCTCGAGTAGCTGGGATTACAGGCAGGCACCATCACGCCCGGCTAATTTT
TTTTTTTTTTTTTTGTAGTAGAAATGGGATTTCACCATATTGGCAGGATGTTCTCGATCT

Chromosome map:

Chromosome 3

FIGURE 3T

ISOLATED HUMAN PROTEASE PROTEINS, NUCLEIC ACID MOLECULES ENCODING HUMAN PROTEASE PROTEINS, AND USES THEREOF

FIELD OF THE INVENTION

The present invention is in the field of protease proteins, recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner AP Press, NY 1998). Also, for a review of the various uses of proteases as drug targets, see: Weber M, Emerging treatments for hypertension: potential role for vasopeptidase inhibition; Am J Hypertens November 1999;12(11 Pt 2):139S–147S; Kentsch M, Otter W, Novel neurohormonal modulators in cardiovascular disorders. The therapeutic potential of endopeptidase inhibitors, Drugs R D April 1999;1(4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann N Y Acad Sci June 1999 30;878:61–72; McKerrow J H, Engel J C, Caffrey C R, Cysteine protease inhibitors as chemotherapy for parasitic infections, Bioorg Med Chem April 1999;7(4):639–44; Rice K D, Tanaka R D, Katz B A, Numerof R P, Moore W R, Inhibitors of tryptase for the treatment of mast cell-mediated diseases, Curr Pharm Des October 1998;4(5):381–96; Materson B J, Will angiotensin converting enzyme genotype, receptor mutation identification, and other miracles of molecular biology permit reduction of NNT Am J Hypertens August 1998;11 (8 Pt 2):138S–142S Serine Proteases The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extracellular matrix. SP are so named because of the presence of a serine residue in the active catalytic site for protein cleavage. SP have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

A series of six SP have been identified in murine cytotoxic T-lymphocytes (CTL) and natural killer (NK) cells. These SP are involved with CTL and NK cells in the destruction of virally transformed cells and tumor cells and in organ and tissue transplant rejection (Zunino, S. J. et al. (1990) J. Immunol. 144:2001–9; Sayers, T. J. et al. (1994) J. Immunol. 152:2289–97). Human homologs of most of these enzymes have been identified (Trapani, J. A. et al. (1988) Proc. Natl. Acad. Sci. 85:6924–28; Caputo, A. et al. (1990) J. Immunol. 145:737–44). Like all SP, the CTL-SP share three distinguishing features: 1) the presence of a catalytic triad of histidine, serine, and aspartate residues which comprise the active site; 2) the sequence GDSGGP which contains the active site serine; and 3) an N-terminal IIGG sequence which characterizes the mature SP.

The SP are secretory proteins which contain N-terminal signal peptides that serve to export the immature protein across the endoplasmic reticulum and are then cleaved (von Heijne (1986) Nuc. Acid. Res. 14:5683–90). Differences in these signal sequences provide one means of distinguishing individual SP. Some SP, particularly the digestive enzymes, exist as inactive precursors or preproenzymes, and contain a leader or activation peptide sequence 3' of the signal peptide. This activation peptide may be 2–12 amino acids in length, and it extends from the cleavage site of the signal peptide to the N-terminal IIGG sequence of the active, mature protein. Cleavage of this sequence activates the enzyme. This sequence varies in different SP according to the biochemical pathway and/or its substrate (Zunino et al, supra; Sayers et al, supra). Other features that distinguish various SP are the presence or absence of N-linked glycosylation sites that provide membrane anchors, the number and distribution of cysteine residues that determine the secondary structure of the SP, and the sequence of a substrate binding sites such as S'. The S' substrate binding region is defined by residues extending from approximately +17 to +29 relative to the N-terminal I (+1). Differences in this region of the molecule are believed to determine SP substrate specificities (Zunino et al, supra).

Trypsinogens

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is tyypsinogen-1 (Guy C O et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-1-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha-2-macroglobulin are not measurable with antibody-based assays (Ohlsson K, Acta Gastroenterol Belg 1988; 51: 3–12).

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, biliary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia; anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton AC (1991) Textbook of Medical Physiology, W B Saunders Co, Philadelphia Pa.; Isselbacher K J et al (1994) Harrison's Principles of Internal Medicine, McGraw-Hill, New York City; Johnson K E (1991) Histology and Cell Biology, Harwal Publishing, Media Pa.; and The Merck Manual of Diagnosis and Therapy (1992) Merck Research Laboratories, Rahway N.J.

Metalloprotease

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium;* Serratia (Miyata et al., 1971, Agr. Biol. Chem. 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from *Aspergillus sojae* (Sekine, 1973, Agric. Biol. Chem. 37:1945–1952). Neutral metalloproteases obtained from Aspergillus have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from *Aspergillus oryzae* has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793–2797).

Metalloproteases have been devided into several distinct families based primarily on activity and sturcture: 1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (*Homo sapiens*), germinal peptidyl-dipeptidase A (*Homo sapiens*), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diaminopimelate peptidase I (*Bacillus sphaericus*), vanY D-Ala-D-Ala carboxypeptidase (*Enterococcus faecium*), endolysin (bacteriophage A118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (*Pseudomonas sp.*), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgA1-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), IAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ss1 (*Sulfolobus solfataricus*), FtsH endopeptidase (*Escherichia coli*), glutamyl aminopeptidase (*Lactococcus lactis*), cytophagalysin (*Cytophaga sp.*), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoartritis (Woessner, et al., J. Biol.Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Burns, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Aspartic protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteases such as the protease from the AIDS virus (HIV) also called retropepsin. Crystallographic studies have shown that these enzymes are bilobed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (*Homo sapiens*), HIV1 retropepsin (human immunodeficiency virus type 1), endopeptidase (cauliflower mosaic virus), bacilliform virus putative protease (rice tungro bacilliform virus), aspergillopepsin II (*Aspergillus niger*), thermopsin (*Sulfolobus acidocaldarius*), nodavirus endopeptidase (flock house virus), pseudomonapepsin (*Pseudomonas sp.* 101), signal peptidase II (*Escherichia coli*), polyprotein peptidase (human spumaretrovirus), copia transposon (*Drosophila melanogaster*), SIRE-1 peptidase (*Glycine max*), retrotransposon bs1 endopeptidase (*Zea mays*), retrotransposon peptidase (*Drosophila buzzatii*), Tas retrotransposon peptidase (*Ascaris lumbricoides*), Pao retrotransposon peptidase (*Bombyx mori*), putative proteinase of Skippy retrotransposon (*Fusarium oxysporum*), tetravirus endopeptidase (*Nudaurelia capensis* omega virus), presenilin 1 (*Homo sapiens*).

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP–2 and MMP–9, respectively). For an overview of this field see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N. Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

Protease proteins, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the protease family.

SUMMARY OF THE INVENTION

The present invention is based in part on the identification of amino acid sequences of human protease peptides and proteins that are related to the protease family, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates expression in the lung, colon, ovary adenocarcinoma, uterus endometrium, lymph Burkitt lymphoma, dendritic cells and human leukocytes.

DESCRIPTION OF THE FIGURE SHEETS

FIG. 1 provides the nucleotide sequence of a cDNA molecule sequence that encodes the protease protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the lung, colon, ovary adenocarcinoma, uterus endometrium, lymph Burkitt lymphoma, dendritic cells and human leukocytes.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence. 37 SNPs, including 3 indels, have been identified in the gene encoding the protease protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein. Utilizing these sequences, additional genomic sequences were assembled and transcript and/or cDNA sequences were isolated and characterized. Based on this analysis, the present invention provides amino acid sequences of human protease peptides and proteins that are related to the protease family, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the protease family and the expression pattern observed. Experimental data as provided in FIG. 1 indicates expression in the lung, colon, ovary adenocarcinoma, uterus endometrium, lymph Burkitt lymphoma, dendritic cells and human leukocytes. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known protease family or subfamily of protease proteins.

Specific Embodiments

Peptide Molecules

The present invention provides nucleic acid sequences that encode protein molecules that have been identified as being members of the protease family of proteins (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates expression in the lung, colon, ovary adenocarcinoma, uterus endometrium, lymph Burkitt lymphoma, dendritic cells and human leukocytes. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein. As indicated by the data presented in FIG. 3, the map position was determined to be on chromosome 3 by ePCR, and confirmed with radiation hybrid mapping.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. As indicated by the data presented in FIG. 3, the map position was determined to be on chromosome 3 by ePCR, and confirmed with radiation hybrid mapping. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

FIG. 3 provides information on SNPs that have been found in the gene encoding the transporter protein of the present invention. SNPs were identified at 37 different nucleotide positions in introns and regions 5' and 3' of the ORF. Such SNPs in introns and outside the ORF may affect control/regulatory elements.

Paralogs of a protease peptide can readily be identified as having some degree of significant sequence homology/identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins. As indicated by the data presented in FIG. 3, the map position was determined to be on chromosome 3 by ePCR, and confirmed with radiation hybrid mapping.

FIG. 3 provides information on SNPs that have been found in the gene encoding the transporter protein of the present invention. SNPs were identified at 37 different nucleotide positions in introns and regions 5' and 3' of the ORF. Such SNPs in introns and outside the ORF may affect control/regulatory elements.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182:626–646 (1990)) and Rattan et al. (*Ann. N.Y. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that protease proteins of the present invention are expressed in the lung, colon, ovary adenocarcinoma, uterus endometrium, lymph Burkitt lymphoma, dendritic cells detected by a virtual northern blot. In addition, PCR-based tissue screening panel indicates expression in and human leukocytes. A large percentage of pharmaceutical agents are being developed that modulate the activity of protease proteins(see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the lung, colon, ovary adenocarcinoma, uterus endometrium, lymph Burkitt lymphoma, dendritic cells and human leukocytes. Such uses can readily be determined using the information provided herein, that which is known in the art, and routine experimentation.

The proteins of the present invention (including variants and fragments that may have been disclosed prior to the present invention) are useful for biological assays related to proteases. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that protease proteins of the present invention are expressed in the lung, colon, ovary adenocarcinoma, uterus endometrium, lymph Burkitt lymphoma, dendritic cells detected by a virtual northern blot. In addition, PCR-based tissue screening panel indicates expression in and human leukocytes.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates expression in the lung, colon, ovary adenocarcinoma, uterus endometrium, lymph Burkitt lymphoma, dendritic cells and human leukocytes. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library frgents, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that protease proteins of the present invention are expressed in the lung, colon, ovary adenocarcinoma, uterus endometrium, lymph Burkitt lymphoma, dendritic cells detected by a virtual northern blot. In addition, PCR-based tissue screening panel indicates expression in and human leukocytes.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates expression in the lung, colon, ovary adenocarcinoma, uterus endometrium, lymph Burkitt lymphoma, dendritic cells and human leukocytes. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; *Zervos* et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the lung, colon, ovary adenocarcinoma, uterus endometrium, lymph Burkitt lymphoma, dendritic cells and human leukocytes. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked inununosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype.

The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amnino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the lung, colon, ovary adenocarcinoma, uterus endometruim, lymph Burkitt lymphoma, dendrtic cells and human leukocytes. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerytrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that protease proteins of the present invention are expressed in the lung, colon, ovary adenocarcinoma, uterus endometrium, lymph Burkitt lymphoma, dendritic cells detected by a virtal northern blot. In addition, PCR-based tissue screening panel indicates expression in and human leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the lung, colon, ovary adenocarcinoma, uterus endometrium, lymph Burkitt lymphoma, dendritic cells and human leukocytes. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the lung, colon, ovary adenocarcinoma, uterus endometrium, lymph Burkitt lymphoma, dendritic cells and human leukocytes. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the lung, colon, ovary adenocarcinoma, uterus endometrium, lymph Burkitt lymphoma, dendritic cells and human leukocytes. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determimng the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 37 SNPs, including 3 indels, have been identified in the gene encoding the protease protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 3 by ePCR, and confirmed with radiation hybrid mapping.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that protease proteins of the present invention are expressed in the lung, colon, ovary adenocarcinoma, uterus endometrium, lymph Burkitt lymphoma, dendritic cells detected by a virtual northern blot. In addition, PCR-based tissue screening panel indicates expression in and human leukocytes. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to norrnal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that protease proteins of the present invention are expressed in the lung, colon, ovary adenocarcinoma, uterus endometrium, lymph Burkitt lymphoma, dendritic cells detected by a virtal northern blot. In addition, PCR-based tissue screening panel indicates expression in and human leukocytes.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates expression in the lung, colon, ovary adenocarcinoma, uterus endometrium, lymph Burkitt lymphoma, dendritic cells and human leukocytes. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG. 1 indicates that protease proteins of the present invention are expressed in the lung, colon, ovary adenocarcinoma, uterus endometrium, lymph Burkitt lymphoma, dendritic cells detected by a virual northern blot. In addition, PCR-based tissue screening panel indicates expression in and human leukocytes. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates expression in the lung, colon, ovary adenocarcinoma, uterus endometrium, lymph Burkitt lymphoma, dendritic cells and human leukocytes.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. FIG. 3 provides information on SNPs that have been found in the gene encoding the transporter protein of the present invention. SNPs were identified at 37 different nucleotide positions in introns and regions 5' and 3' of the ORF. Such SNPs in introns and outside the ORF may affect control/regulatory elements. As indicated by the data presented in FIG. 3, the map position was determined to be on chromosome 3 by ePCR, and confirmed with radiation hybrid mapping. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic, acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein. FIG. 3 provides information on SNPs that have been found in the gene encoding the transporter protein of the present invention. SNPs were identified at 37 different nucleotide positions in introns and regions 5' and 3' of the ORF. Such SNPs in introns and outside the ORF may affect control/regulatory elements.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that protease proteins of the present invention are expressed in the lung, colon, ovary adenocarcinoma, uterus endometrium, lymph Burkitt lymphoma, dendritic cells detected by a virtutal northern blot. In addition, PCR-based tissue screening panel indicates expression in and human leukocytes. For example, the kit can comprise reagents such as a labeled or labelable nucleic acid or agent capable of detecting protease nucleic acid in a biological sample; means for deterinining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention flrter provides nucleic acid detection kits, such as arrays or microarrays of nucleic acid molecules that are based on the sequence information provided in FIGS. 1 and 3 (SEQ ID NOS:1 and 3).

As used herein "Array" or "Microarrays" refers to an array of distinct polynucleotides or oligonucleotides synthiesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the fall length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention. FIG. 3 provides information on SNPs that have been found in the gene encoding the transporter protein of the present invention. SNPs were identified at 37 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd.* ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd.* ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301– 315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed, Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced orjoined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is-difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the tmnsgenic sequence. This includes intronic sequences and polyadenylation signals, if not already included. A tissue-specific regulatory sequence (s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carring out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:

(a) a nucleotide sequence that encodes a protein comprising the amino acid sequence of SEQ ID NO:2;

(b) a nucleotide sequence consisting of SEQ ID NO:1;

(c) a nucleotide sequence consisting of SEQ ID NO:3; and (d) a nucleotide sequence that is completely complementary to a nucleotide sequence of (a)–(c).

2. A nucleic acid vector comprising a nucleic acid molecule of claim 1.

3. A vector according to claim 2, wherein said vector is selected from the group consisting of a plasmid, vius, and bacteriophage.

4. A vector according to claim 2, wherein said isolated nucleic acid molecule is inserted into said vector in proper orientation and correct reading frame such that the protein of SEQ ID NO:2 may be expressed by a cell transformed with said vector.

5. A vector according to claim 4, wherein said isolated nucleic acid molecule is operatively linked to a promoter sequence.

6. A host cell containing the vector of claim 2.

7. A process for producing a polypeptide comprising culturing the host cell of claim 6 under conditions sufficient for the production of said polypeptide, and recovering said polypeptide from the host cell culture.

8. An isolated polynucleotide consisting of a nucleotide sequence set forth in SEQ ID NO:1.

9. An isolated polynucleotide consisting of a nucleotide sequence set forth in SEQ ID NO:3.

10. A method for detecting the presence of a nucleic acid molecule of claim 4 in a sample, said method comprising contacting the sample with an oligonucleotide comprising at least 20 contiguous nucleotides that hybridizes to said nucleic acid molecule under stringent conditions, wherein the stringent condition is hybridization in 6×sodium chloride/sodium citrate (SSC) at about 45° C., followed by one or more washes in 0.2×SCC, 0.1% SDS at 50–65° C., and determning whether the oligonucleotide binds to said nucleic acid molecule in the sample.

* * * * *

SEQUENCE LISTING

```
<160> NUMBER OF SEQ ID NOS: 4

<210> SEQ ID NO 1
<211> LENGTH: 1247
<212> TYPE: DNA
<213> ORGANISM: Human

<400> SEQUENCE: 1

gccatggtgg ggcagaggtt gggaagatgg cgtggcgagg ctgggcgcag agaggctggg     60

gctgcggcca ggcgtggggt gcgtcggtgg gcggccgcag ctgcgaggag ctcactgcgg    120

tcctaacccc gccgcagctc ctcggacgca ggtttaactt ctttattcaa caaaaatgcg    180

gattcagaaa agcacccagg aaggttgaac ctcgaagatc agacccaggg acaagtggtg    240

aagcatacaa gagaagtgct ttgattcctc ctgtggaaga aacagtcttt tatccttctc    300

cctatcctat aaggagtctc ataaaacctt tattttttac tgttgggttt acaggctgtg    360

catttggatc agctgctatt tggcaatatg aatcactgaa atccagggtc cagagttatt    420

ttgatggtat aaaagctgat tggttggata gcataagacc acaaaaagaa ggagacttca    480

gaaaggagat taacaagtgg tggaataacc taagtgatgg ccagcggact gtgacaggta    540

ttatagctgc aaatgtcctt gtattctgtt tatggagagt accttctctg cagcggacaa    600

tgatcagata tttcacatcg aatccagcct caagtgttat ttccaatttt gtcagttacg    660

tgggtaaagt tgccacagga agatatggac catcacttgg tgcatctggt gccatcatga    720

cagtcctcgc agctgtctgc actaagatcc cagaagggag gcttgccatt attttccttc    780

cgatgttcac gttcacagca gggaatgccc tgaaagccat tatcgccatg gatacagcag    840

gaatgatcct gggatggaaa ttttttgatc atgcggcaca tcttggggga gctctttttg    900

gaatatggta tgttacttac ggtcatgaac tgatttggaa gaacagggag ccgctagtga    960
```

-continued

```
aaatctggca tgaaataagg actaatggcc ccaaaaaagg aggtggctct aagtaaaact   1020

gggattggac agtagtggtg catctggtcc ttgccgcctg agagccccag gagacatcgg   1080

ctagagtgac catggctatg ctcccgtctg gaagatgcca gcatctggcc tcccactgtt   1140

ttcagctgtg tcccccagtc cgtgtctttt tagaatgtga atgatgataa agttgtgaaa   1200

taaaggtttc tatctagttt gtaaaaaaaa aaaaaaaaaa aaaaaaa                 1247
```

<210> SEQ ID NO 2
<211> LENGTH: 329
<212> TYPE: PRT
<213> ORGANISM: Human

<400> SEQUENCE: 2

```
Met Ala Trp Arg Gly Trp Ala Gln Arg Gly Trp Gly Cys Gly Gln Ala
 1               5                  10                  15

Trp Gly Ala Ser Val Gly Gly Arg Ser Cys Glu Glu Leu Thr Ala Val
            20                  25                  30

Leu Thr Pro Pro Gln Leu Leu Gly Arg Arg Phe Asn Phe Phe Ile Gln
        35                  40                  45

Gln Lys Cys Gly Phe Arg Lys Ala Pro Arg Lys Val Glu Pro Arg Arg
    50                  55                  60

Ser Asp Pro Gly Thr Ser Gly Glu Ala Tyr Lys Arg Ser Ala Leu Ile
65                  70                  75                  80

Pro Pro Val Glu Glu Thr Val Phe Tyr Pro Ser Pro Tyr Pro Ile Arg
                85                  90                  95

Ser Leu Ile Lys Pro Leu Phe Phe Thr Val Gly Phe Thr Gly Cys Ala
            100                 105                 110

Phe Gly Ser Ala Ala Ile Trp Gln Tyr Glu Ser Leu Lys Ser Arg Val
        115                 120                 125

Gln Ser Tyr Phe Asp Gly Ile Lys Ala Asp Trp Leu Asp Ser Ile Arg
    130                 135                 140

Pro Gln Lys Glu Gly Asp Phe Arg Lys Glu Ile Asn Lys Trp Trp Asn
145                 150                 155                 160

Asn Leu Ser Asp Gly Gln Arg Thr Val Thr Gly Ile Ile Ala Ala Asn
                165                 170                 175

Val Leu Val Phe Cys Leu Trp Arg Val Pro Ser Leu Gln Arg Thr Met
            180                 185                 190

Ile Arg Tyr Phe Thr Ser Asn Pro Ala Ser Ser Val Ile Ser Asn Phe
        195                 200                 205

Val Ser Tyr Val Gly Lys Val Ala Thr Gly Arg Tyr Gly Pro Ser Leu
    210                 215                 220

Gly Ala Ser Gly Ala Ile Met Thr Val Leu Ala Ala Val Cys Thr Lys
225                 230                 235                 240

Ile Pro Glu Gly Arg Leu Ala Ile Ile Phe Leu Pro Met Phe Thr Phe
                245                 250                 255

Thr Ala Gly Asn Ala Leu Lys Ala Ile Ile Ala Met Asp Thr Ala Gly
            260                 265                 270

Met Ile Leu Gly Trp Lys Phe Phe Asp His Ala Ala His Leu Gly Gly
        275                 280                 285

Ala Leu Phe Gly Ile Trp Tyr Val Thr Tyr Gly His Glu Leu Ile Trp
    290                 295                 300

Lys Asn Arg Glu Pro Leu Val Lys Ile Trp His Glu Ile Arg Thr Asn
305                 310                 315                 320
```

```
Gly Pro Lys Lys Gly Gly Gly Ser Lys
                325
```

<210> SEQ ID NO 3
<211> LENGTH: 19736
<212> TYPE: DNA
<213> ORGANISM: Human

<400> SEQUENCE: 3

```
cgaggtttct tcatgttggt caggctggtc tcgaactccc gacctcaggt gatccgtccg     60

cctcagcctc ccaaagtact gctgggatta cagacgtgag ccaccgcacc cggcctttat    120

ctttcatttt ttttcatgta ttttccttta ttttaatcac tttatccaga aacatatcct    180

cgtcttgaca gtgctgtggt gcctgtggtt tccagaagct gggtgtgctg tgtgtctgtg    240

gtttgaggaa gttgcccatg gaactgacag aggaagcaga gtagtcgttg ccatttttca    300

gcctagtagg caggatcagg gaccccatct tgctctcttt gccttgaacc acaattagaa    360

taaaacacca aagccctgac tgatcatgat catagcaatc cgatctttat gatcatggcc    420

agaccattct caggtcgtct ttaccctaag atatcaatca ctgggtatga caacctagac    480

ctaagggtgc actctgggta gtaaagatga ttaactctcc caaaggaatc taaggaatcc    540

agagcaacac gaatcactgc tctcttccta tagggtaaac ctcccaagac tccagtccct    600

gtgaggaggc tctgcccgcc tgcccttccc agggttccag gctccacatt gggaggtgta    660

cacagtgctc ttcgctcttc attgccttgt gtatgatccc ttttcccatc tttgcataaa    720

tgctgtccct ctcaccatct ttaaaagagt tctgggtaat tatttaccaa aggtggtata    780

atgctgtcac agtccctgct agtgagacat ctgatacaac tgatggaatc agttcaacaa    840

aatgcagtaa aattttattt aatgtactac ggagaaagaa aaaatgctac cagttataag    900

atgcatcctg atttcagata ttaaaatgga aaaaatgtct taagatctgt gaaaaatgta    960

gcttcctttc ccacctctca agtgggagag caaaaactgg acagactaga aatgccaggg   1020

gctagctgag aaccttacag aatgagcaac tgcggaagcc acaggtaaca ccgagatgta   1080

gatcagctgc cagggacaag acaaagaatg ttttctaaag taaatcctct taccagtatg   1140

ttattgaaat cagtccttat tggcatcgaa gaaggtgaaa gtgctacttg cctgttgcct   1200

acagagactg gaggaatgac aaatgtttaa attattttaa ttcaacaagt agaggaatac   1260

ctgctatgtg aaggagttgt ggcaattcat aaaattaata tattttttga agtttgtagt   1320

tttcaataat aatttcttat ctaaaatgta acaagttaat tatattatcg aataaacctc   1380

aatttcgtag tactaacaac atcaacactt acagaaaaag gaaagtcact caactcccac   1440

atgtaaacag actttagaag cagttgcaga ggttttctaa attatccctg aattcctatc   1500

acatgactat ttttctcaga catgttgacc ttcacctaca cagatgactc acatatgttt   1560

ccataagctg gcagtaagtt taagaagcat accatgccct gaggaaaaag aagtaatgtt   1620

agctcttcta ctcttggcca aagaacctaa ttctgtatat tacttctgtc tttggtttgg   1680

ctattataga caataaatta ttgatctgat tataattgag aaaagtaagc tcttctaaag   1740

aagtaaaata tggatctagg gaaaggaagt tagctcccag agcatttaca atttcccagg   1800

aattctgtga ctttaccaac cctaggcagt gctgatactt taaaagcatt catttcactt   1860

gctttttttt ggctcacccc ctatccccca ggtatacagt actcttacat aattgtggaa   1920

gaatcttaca agggggtaat gtagatcaga ctttcctgct ttcattttta acctccctaa   1980

attataaata tttattttgt aggtattata gctgcaaatg tccttgtatt ctgtttatgg   2040
```

-continued

```
agagtacctt ctctgcagcg gacaatgatc agatatttca catcgaatcc agcctcaagt   2100
aagtctaact tgtgtgaatt tattttaagg tagaaataat atgaaagaaa tatgctttag   2160
ttaatggaag tgctgtaaaa aagacgaatt acctatcaat agctacaagc aaaatgcaga   2220
ggataggctg taagctcctt cactgaggac agggacctca cctctctttt tctttttctt   2280
tgtttttttt gagacggagt cttcctctgt tgcccaggct ggagtgcagt ggtgcagtct   2340
tagctcacta caacctccac ctcccaggtt caagtgattc tcctgcctca gcctccctag   2400
tagctaggat tacaggtgcc cgccaccaca cccagctagt ttttgtattt ttaatagaga   2460
cagggtttca ccgtgttgga taggctgttc ttgaacacct gacctcaggt gatctgcctg   2520
gctcggctgg agtgcagtgg cgtgatctca gctcactgca agctccgcct cccgggttca   2580
tgccattctc ctgcctcagc ctcctgagta gctgggacta caggtgcccg ccaccacgcc   2640
ccgctaattt ttttgtattt ttagtagaga cggggtttca acatgttagc caggatggtc   2700
tcgatctcct gacctcgtga tccgcccgcc tcagcctccc aaagtgctgg gattataggc   2760
gtgagccact gcgcccggcc aatttacttt ttattttatt ttattttatt ttttgagaca   2820
gggtcttgct ctgttgccca ggctagagtg cagtgatacg atcttggctc actgcaacct   2880
ctgcttctca ggctcaactg atcctcccac ctcagccccc aggagctggg actacaggtg   2940
catgccacca tgcccagcta attttttttg tttttagtgc agatgaggtc ttgccatgtt   3000
gcccagactg cttatttttt tctaatcaac ttttgccata aggacaagtt gctttcattg   3060
aactgagagt ttttattggt tgcttactaa gtagaaaaga atatttatta agacagcttt   3120
ttgtcacttt taaaaatgat gtcttaagct gggcatagtg actcacatct ataatcccag   3180
cacttgggga ggctgaggca ggtgaactgc ttgagctcag gagttcgaga ccagcctggg   3240
aaacatggtg aaaccccatc tctactaaaa atacaaaaat tagttgggca tggggtatgt   3300
acctgtggtc ccagctactc agggaggctg aggtgggagg atcacttgag cccttgagcc   3360
tcaacttgag gaagttgagg ctgcagtgag ccaagatcag tgccactgca ctccagcctg   3420
gggcgacaga gcaagactct ctccaaaaaa aaaaaaaagt cttaaaaata gctgtttttg   3480
ttttccatgt ttgtttcata aatttttttt tttttttttt ttttgagata gagtctcgct   3540
ctatggccca ggctggagtg cagtggctca atcttggctc actgcaaact ctacctcctg   3600
ggtccaagtg attctcccgc ctcagccttc cgagtagcag gaattacaaa cgtgcgccac   3660
cacacctggc taatttttat atttttaata gagatggggt ttgactatgt tggccaggct   3720
ggtcttgaac tcctgactta gtgatccgcc tgccttggcc tcccaaagtg ctgggattac   3780
aggcgtgagc cactgcgtcc ggcctaattt taaaagttta aaatggataa tttttattgg   3840
ctgtgtgttt catgattacc agactatgtt tctctctctt gtagaggtcc tttgttctcc   3900
aatgttgctg tcaacattca gtcatttctc cttatttcac atggcagcaa atatgtatgt   3960
tttgtggagc ttctcttcca gcatagtgaa cattctgggt caagagcagt tcatggcagt   4020
gtacctatct gcaggtaata tgctttaatc tcggggcctt tgagagtata agcactctaa   4080
gctatctgca gaacggacaa agggaatgat tactgccata ttctacacgt agtgagtgct   4140
cagaacatat ttgtttctca cagtgtatgt agagaaggga gccacagatt ggtggagatg   4200
ttgccttttc tgttcatttt gctgatttct tcttacatat gaattatgtg ggtatgttta   4260
attttaagtt aggataaaca ggcgttaagt aagggttagt gtagaattta agcatgtcat   4320
ttttgtaatc tcatcgggcc ttgatttcat tagtttaggc cctccatttt atagatagtg   4380
gttcccagac ttcccggctg cctcaatctc ctgggtcttt gttaaataac cttaagcaag   4440
```

-continued

```
ctcatttccc ccagtgtgtt cagttcacag aaagctttaa atcagagcta tacaatatga   4500
ttgtcaagag tgagtttgtt ctgtcttctt tgcaagaatg tagcagggaa ccacttccta   4560
gccatggtct tgaagatggt atcgtttctt atttcagtta ggaaattctc atgcatgaat   4620
ccaggtccct agatgctgct aacgtgacag ttggtcaaat tttacttacc tctctgtttg   4680
taaaatgtac ttacttaata caatataaaa attaatttct aaaatctcta catttagaaa   4740
cagtatatct ggcagttgtg ctgtgatgta gtgaaaaaca ctaagcttgg cgatagaccc   4800
aggttcagat cctatttcta ctaccagctg agtgatgttg caaaaatgac taaacctcat   4860
gatacttacc tcctcatgac aaggggttaa agaaaggact acataaaagc atctaccaca   4920
agccccagag tagatgctta attagtgttc atcgaatact tatgtgtatc tagtccttca   4980
aaaaaagaag ctgagcattg tgtttggctt gtaagataag tgtatagttc tttcccaagc   5040
actagttatg ttgtagttac agagggtctg tttcagatac attaattcct gctccatagg   5100
aggtttttaa aaatgagcca cgttgactca aatggcactg aagccaaaga gacttacggg   5160
atcatccagt ctgttgtccc accccagata ttctgatttc gtgtgtctgg agtacagcca   5220
gagaatatac tcttgggaat gagtcttcat gttatagttg aggaaaatgg taactgagaa   5280
gtggagtgaa tgaccgtgtc gctcagcaga tcatgcagca ggtcagactt ttcatcccct   5340
gtaaagtcgc tgaaatgata ggcaggagaa gtattcatgc ccgtaccctc acagtgatcc   5400
agattgaaac ccgacactgt ttatctgtgt agaaatcaga aatgaaaacc attttcatgg   5460
ctggatgtgg tgccgcacgc ctgtaatccc agctactcag gaggctgggg gacaagaata   5520
acttgaaccc ggtaggcaga ggttgcagtg agccaaaatt gtaccactgc acttcagcag   5580
ccggggcgaa agagtgaaac tctgtctcaa aaaaaaaaaa aaagaaaaga aaaaaaaaag   5640
taaaccattt ttatacctca cttaaattat tgtaatgtga cttgtttttc aggtgttatt   5700
tccaattttg tcagttacgt gggtaaagtt gccacaggaa gatatggacc atcacttggt   5760
gcagtaagta tttctattgt aaattttttt taatttaatt tttaaattta ctttgaaata   5820
agtttagact tagaagaatg ttgtaaaatt gataagtagg ttctcatata cccttcaccc   5880
tactgttaac taacatcgaa accaagaaat taacattgaa acaatacagt tgactaattt   5940
agaatttata catttgtaaa gctttgtaaa tgtccggcta tagcttttaa ccattggtca   6000
tatatatatg tttaccagag cagagtatat ctcagaacag taagtgtgca atcctcgtaa   6060
accagagagc ctaatccagt attggaagat tctaattata gatttgaatc tggtacttta   6120
tcctcctatt tagtcaatat tggagtgcct actaggtgct atgctagagc ctggggataa   6180
cagctggtga gcaagatgat cacgattatt tgtgttggtt ttagaaagtg gggaacaaca   6240
acaacaaaaa aggctcctgc cctcagagct cttatattct ggatgcttaa aaaaattttt   6300
cttaggctgg atgcagtggt ttacacctgt aatcccagca ctttgggagg ccaaggtgag   6360
aggatgagcc caagaattcg aaaccagccc tggtaacata ccaagatcct atctgtacaa   6420
aaaaatttaa aaaattaact gggggtggtg gcttatgccg gtagtctcag ctactcagga   6480
ggctgaggaa ggaggatagc ttgagcctag gaggttgagg ctgcggtgag ctgtgattgt   6540
accactgcac cccagcctgg gtgacatagc aagaccctat ctcaaaaaaa aaattttttt   6600
ttaagtgtgt tttgaggctg ggtgcagtgg ctcacacctg taatcccagc actttgggag   6660
gctgaggtgg gcagctcact tgaggtcagg agttcaagac cagcctggtc aacatggtga   6720
aaccctgtcc ctcctgaaaa tacaataatt agccaggtgt ggttgtgcat gcttgtaatc   6780
```

-continued

```
ccagctactc gggaggctga ggcaggagaa ttacttgaac ccagcgggta gaggttgcag   6840

tgagctgaga ttgcaccact gcactccagc ctgggtgaca gaacaagacc ctgtctcaca   6900

gaacaagacc ctgtctcaaa gaaaaaaaat ttttttaagt gtcttttgag tttaatggca   6960

gatttctggg cacatggaaa tctttatgta atatttcctt acacattcag tttgtactta   7020

tttaaatact aattcattta aatgcattca aatagggaat ttcctattta aaggaactct   7080

aaaaaggtca attttgaaaa gaattcttat gtaaaataac cattccctaa tttgtatgtt   7140

ccccaaattt gtttacactt aattttccta gtgaggcctg tgttctgtcc tgtgaccaca   7200

tgctttctta agcctccttt tttcccttcg tggaatgttt attttcttta tacaatttcg   7260

ctctgatata atttatatat ttcgaatcat attgtctacc tcattcaaca gctaagcacc   7320

taatatatga aggcagtgaa gaccactagg atgaatcaga gactcagaat tcgaatttag   7380

ctggggagaa aacatgcaca catctaatac acactgaaag gaatgaggat tctctagagg   7440

actttggggg ctctaagagt gaagagacct ttctaattag ctgaaaggac ctgcgagggc   7500

attttgatgt gctcttggac agctgttgtc ctcatcttat agataagaaa ctgaagtgca   7560

aacttaatga agtatggcag taaggtattt ggagttagag tgggggtgaa tcctggttct   7620

gctacttacg tgtgatttct aggacatatt actgaacttc tctgaatttc agtttccctt   7680

tataaaatgg ggataacacc atctatttct gaggtgcaaa gcaagtacat ttagagtgct   7740

tagcacaata agaagcacat ggtaagaaat gtggacatgg tagttcctgt tcagtcatca   7800

aaatcctaca gcgccgtggt aggataacat tatccccaaa tatcttaatg aatctgtgat   7860

taaaattcaa ggaaattaaa tcaccaggta taatggcatt tttaatgaga aatctgggaa   7920

aaaaacacca ttaacaaagt tgtgttgtta caaaatgtaa agcgttagtc ctcttggttt   7980

agtgagacgt tataagatgc aggggacagc caggcacagt ggctcacgcc tgtaggccca   8040

acactttggg agccacggca ggaagatcac ttgagcccag gaggtttgag actagcctgg   8100

gcaacaaagt gagaccccat ctctacaaaa aatttcaaaa ttaagccggg catggtggca   8160

tgcacctgta atcctaccta ctcaggagag gtgggagggt gggaggaatg cctgagccta   8220

ggagggtgag gctgctgtga gccatgagca tgccactgtg ctccaacctg gacaacatag   8280

cgagacccca tctcaaaaaa aaaaaaagaa agttgaatgg gactgttaaa atatgtttgt   8340

aaattactgt attggtacta tcctggataa tttttaaact tttctgtaga gacagggtct   8400

ccctatgttg ccaaggctgg tctcaaactc ctgggctcaa gtgatcctcc tacctgggcc   8460

tcccaaagtg ttgggattac tggtgtgagc cactacaccc ggccaattgt cttttcttat   8520

tcaagttgag atttttctgg ttcttgatat gatgagtgat ttttcagttg aagcctgatc   8580

attttagata tgatgagact ttggatctta ttgaaatctg ctgtttcagt ggtcttcctc   8640

tgacactgtt ctgatgagga gagggggtgc cgtgactcgt tactgctggg tgtaggagta   8700

gacgtccagg ttcctcactc agccgccttt gcctcctgag tgataggggc tcttgtcact   8760

gcagggcagg gatgggagct gagggcgtgc aggctaccta gtgtgcctct gctaatgtcg   8820

ctgtggctag gaggagcaag ggtgcttctt tccgctgaca ccgcctgtta ggcgtattgg   8880

gatgcctcat tacagtgtgg caagggtggg agtctaggct ctgctcagcc tttgctgggc   8940

acccgtttct ctaaatattg tctaaaaggt ctcttttgct aggctatctt tttttggtcc   9000

ttgactagag agaacatgtt gagggatgat cgatatgagg ccaaaagaaa gcccagggaa   9060

ctcaccacca caacattgat tgaatctcag gcttcctagc tggtccgctt tcctctctct   9120

tcctttcaca gtcctcttac atttgtttca tatgtaacac ccagggtctt tagctgtact   9180
```

-continued

```
tagcttttgt aagcagaggg agcagattca cttaaattat aataccaaat aaagttaaaa   9240
aacataagta tgatagattt gaagattata tagatacaga aaaatgtttg tgagcccagg   9300
cgcagtggct cacaactgta atcccagcac tttgggaggc cgaggtgggt ggatcacttg   9360
aggccaggag ttcgaaacca gcctggccaa catggtggaa ccccatctct actaaaaata   9420
caaaaattag ctgggcatgg tggtgtgtac ctgttagtcc cagctacttg gcaggctgag   9480
gtgtgagaat taacttgaac ctgggaggcg gaggttgcag tgagatcgtg ccaccgcact   9540
ccagtttggg caatagcgag actctgtctc aaaaaatata tgtttatgaa ataagtaaaa   9600
aaaaatcaga tgtgcatatt gattacaggt atataaccag tacataaaaa tattgatgga   9660
gaacaaaaga ccttcacctc ttcccatgga cccacacctc ttaggtctgt tggatcaggg   9720
ttcatgactc actgtactta aactgtgtat gaatgtgagc gttttctgag aagagaaggg   9780
ttcattttca ttaaattctt ctttctgact cgaaaaagtg aaaaaagtct ctctgcatgg   9840
gagtaagccc aaatatttgt caaaaaacaa gttgtgattt attcagacat ataaatattt   9900
aaatttatat aaaagccaca tcgagaaaat tctagaagga tgatggaact gtgtatgtaa   9960
taattacaat aagttataat cacaaaaaaa ccagcgttcc atggaattgt acagataacg  10020
acaatttttt ttaacagatg gagaataatc atctatggaa tagtagttta gaagaacttc  10080
atagaatttt tttttttttt tttttttttt ttttttggag agggagtttc gttcttgttg  10140
cccaggctgg agtgcaaagg tgcgatctcg gctcgctaca acctctgcct cccgggttca  10200
agcgattctc ctgcctcaac ctcctgagta gctgggatta caggcatgca ccaccatgcc  10260
cagctaattt tgtattttta gcagagactg ggtttcttca tgttggtcag gctggtctcg  10320
aactccagac ctcaggtgat ctgcccgcct cagcctccca aagtcctggg attacaggtg  10380
taagcgactg tgcctggcag aacttcatag aattttaatg ctcttttata tcaactaatc  10440
aaattatatt tgcttcattt tggggaaacg tgtaattttg atttgttttg gggttttttt  10500
gagataaagt gtcactctgt cgcccaggct ggagtacagt ggctcaatct tggctcacca  10560
caacctcagc cttccgagta gctgggacta caggcgccca ccaccacgtc tggctaattt  10620
ttgtgttttt agtagagacg gggtttcact atgttggcta ggctggtctt gaactcctga  10680
cctcaggtga tccacctgcc tcggcccctc agagtgctgg gattacaggc gtgagccacc  10740
gtgcccggct acaattatag tctcttgcac agaagccagc ttggtcaaaa ttcaggtctt  10800
cttgggtcct ccttttgagg agtgttcatg ctgtccttcc atcttgcagt taccctgact  10860
tctaagaatg caacccgagc ttgtttccct gttgaggcca cttggcagtt atatgaggga  10920
ctggggacat ctgagatctc tgggactcat aataattttc tttaaagttt tagtaattcc  10980
ccaaatgtaa gataatcttg tattctgaag caacccgtca catagaagac attaagaaaa  11040
cattgattaa gagaggtaga tgctattttc cagaaacaac cgtttttata tgaaaaggta  11100
ggaacctttc tttttaatga taggggcttc tttcaaaagt tattttgctc ttaggtgtct  11160
tttttttttt tttaaacatc tcattcataa ataattaaaa acttatggga aagttgcagg  11220
gaatagtaca gaggactccc ataaagtctt ttttgtttgt ttgttttgtt ttgttttgag  11280
acagagtctc gctgttttac ccaggctgga gtgcagtggg acaatctcgg ctcactgcaa  11340
cctctgcctc ccgggttcaa gcaattctcg ggccttagca tcctaagtag gtgggattat  11400
aagcatccgc caccacgccc agctaatttt tttttttttt tttttttttg tatttttagt  11460
agagacgggg ttttaccacg ttggtcaggc tggtctcaaa ctcctgacct caggtgatcc  11520
```

-continued

```
acctgcctcg gcctccaaaa gtgctgggat tataggcgag agccactgca cccagcccca  11580
tgtagtcttt ttaaaaagca ggcaactcag gtttactagt taacatgcaa aaaactgcac  11640
atatttaaag tttggtaagc tttgacatgt agacacccgt gaaaccatca ccacactcaa  11700
gatcatggac atattcatcc caaaagcttc ctagtggtca ctccttcctg cccctcctct  11760
acccctggcg acaacttacc tacttctact aaagataaat tagtttgcaa atggaaccat  11820
acagcatata ctagtatttg ttgtcctggc ctcatttact ctgtataatt actttgagac  11880
tcatccatgt tctgtgtatc agtttattcc tttattattt ttgagacagg gtcttactct  11940
gttgcccagg caggagtgca gtggtgcaat catagctcac tgtaaccttg acctcctggg  12000
cttaagggat cctcatgcct cacaatgtgc tggaattaca ggcgtgagcc accacactgg  12060
caatgttttg tttctttatg aagatgaata aagatttcac atgaattttt taagatgaaa  12120
catgcttcat gcatgcaggt ttctttgggc gtattcatgc ccactccctc tggttggagc  12180
tttgtcagag aagtgtgagc agttctttcc taggccatag gtgaaagatg cgcatgacac  12240
gcttagcact gtccttgcgg ttcatgaggc acatacatct tactgccccg tagtaaaaat  12300
tcagtctttc caagcgatta ctgtgtgaag gacatttagt tccttcacct attattgggg  12360
acataagtaa ctgaaagctt tgaagctttg tgctcaccta gaaatgtgca gcatgtaaac  12420
tttctagaaa atgtgctgct ctttagacct tgtagccact aagcagttgc atattgagtt  12480
tcccattctc cctgctgtgt tactttgcag tctggtgcca tcatgacagt cctcgcagct  12540
gtctgcacta agatcccaga agggaggctt gccattattt tccttccgat gttcacgttc  12600
acagcaggga atgtaagtat ttttatgaag tgcagtgctg gggatagtgg tgatgttttt  12660
atgttgagtg ggttcttgcc cttaagttag aaatgtcagt gctggagcaa tcacagttgt  12720
gccgcttgtt tcttgctgcc tttcaggccc tgaaagccat tatcgccatg gatacagcag  12780
gaatgatcct gggatggaaa ttttttgatc atgcggcaca tcttgggggga gctctttttg  12840
gaatgtaagt ttgagtgtaa ttgattgcta aactgcttcc ttgggtcatg cgctcctcct  12900
accccagcct cacccctacc ccccatcccc atggcagaga cattgaacta tgcaacggaa  12960
gcagaagcag gtgggcttgg gagggtgagg aaacctcaac atggcttgct ttgggtttac  13020
ccagcatacc tggctcattg tagagacagt ctgtgccttt accctacgct taaccttaag  13080
ttgccccaac tgttggcctg ttattcccag cccctctta gaagactgca gcctggcccc  13140
cagtctatgc tgacatcttc tttttcccct tcagactttc ctgccctcct ctcccctgcc  13200
tggcgtccca ccctgctacc ctgacctctg tctcgccagt gctatttaga catgctgagt  13260
tggcggagcc attgctctgt atgactggag tagaggccgg tgactgcaaa ccaatgtgga  13320
ccacttactg agtacccgct gtatgcaggc accaagctag ttcccttatg ttatactatt  13380
actactccca ttttactgat gggaaactga ggctcagaca tcatcttccc caggccaaac  13440
agctcttcaa tagcagagca gagctgtaaa cccacctcta taagcccttt ccaccccccac  13500
cacaccatat ggaattggtt gctaaactgc ttccttgggt cacagcaaat ggcattgtgg  13560
ttacaagacc ttccacgtgt gcttcaaaca atggggtttt gcctagacta gtgcttagta  13620
gtaactgtat cacggaaaca cggtcaggac tcttggcgtc catctgatcg tgggagaccc  13680
gtcagcatga gctggatccc ctcgggggcct gtcttttctt acataaatgt tgccttttgc  13740
ccttacttgg tttttatttt gttccgcgac aatggaaaac ttaatttttt tttttattaa  13800
aaagaaaaat ctattctggc caggtgcagt ggctcacgcc tgtaatccca gcactttggg  13860
aggccaaggc aggcggatca caaggtcagg agatcgagac catcctggct aacacagtga  13920
```

-continued

```
aaccccgtct ctactaaaaa tacaaaaaac ttagccgggc gtggtggcgg gcgcctgtag  13980
tcccagctac tcgggaggct gaggcaggag aatggtgtga acccagaagg cagagcttgc  14040
agtgagccga gatcacgcca ctgcactcca gcctgggcga caaagtgaga ctctgtctca  14100
aaaaaaaaaa aaagaaaaat ctattctaag tgaagcagtt tttcccagta ggtggcagaa  14160
ctaaatgcca ttatgccatt tataatttta agtgattaaa gaggagtagt atgtagtata  14220
tgcaaggtct agctctaaca gcagtgcagt ataaatagta gaaactgacc tgatattaca  14280
gtatgagaaa catgaagggg ttctgttttg tgagctctaa atttatcttc catgtatact  14340
tcaaggctct tctccccagt agatttttat tcatctgaac tataattagg tggccttttt  14400
ccattctgaa aataattgga tcaaatgcat tttaaagtcc agggtctgaa aggtggagga  14460
atcctttctc tttactgttt ctaatttaaa ctccttttca tttactagat ttcagtcatg  14520
tccagaattc atcttttcta aaagctttaa tctagattta gaaatctaaa atcttttatt  14580
tatttttttt tcgttgaagt gccctgattt tgttggtggt aaagactcca ttagtatcca  14640
cttatacatt tccctgactt tgcctctgac caaaccttac agtattcaca ttgtactgtt  14700
gcaataataa tagctaacat attaatacac tgaatatttg ctgtgtgcct aagctaagga  14760
tttaattctc ttaaaatcct gtgaggtatt ttattttaca gaaaaagaaa ctgcttaaag  14820
aaagtaactt atccaggtca cacaagtaac aattgcagag ctggagtttc agatgagggc  14880
tggcttgcgc tgccgctaca gaaaagagtg ccctagaaat cggtcatctt gcatttcccg  14940
attttagttt agccaaatga aaaattcctt ttggatttat gagtataatc agacagtata  15000
cctgtgaaat taaagtattt gactctttgc ttgaaataag taggttaaaa agatttgggt  15060
ggccgggcgc agtggctcac gcctgtaatc ccagcacttt gggaggctga ggcaagtaga  15120
tcatttgagg tcaggagttc gagaccagcc tgaccaatat ggggaaacct cgtctctact  15180
aaaaatacaa aaattagccg ggcgtggtgg tgcatgcctg taataccagc tacttggagg  15240
ctgaggcagg agaatcactt gaagccagga ggcagaggtt acagtgagct gagatcacgc  15300
cactgcactc cagcctgggc aacagagcgc gactctgtct aacaacaaaa aagatttggg  15360
aaaacacttt attaatgaag agttcctgac aaagtgattt ttttggggag aatttttata  15420
attgcatttg aatattaggg tgctcctttt tctctcattc taaattcacc agagacttaa  15480
gcacagagaa tttttattac atgcctgtta attaatgtgt ataatcagat tttaactata  15540
tttagtgaat attaagattc aggtacaaat caagcccttt ataattaaac atacacattc  15600
agaacatttt taaaatatta aaacattaaa ctgctcttct cacccactcc aagtcaaata  15660
gcattttttc agtcaggtgt ctgggagctc gatgcaagat aacaaaatct ggtctctgcc  15720
tcagggaaca tgaaatctgt ttggggaagc cagagcaaaa ataaaggttt taatagcaag  15780
ctctcactaa ctgcccctgg aaatccaccc cacatcctcc aggaagcctt tctctacccc  15840
cagtgccctc aggagcttct ccaaggcagg cccttcccag agcgcagtgt gctccccagc  15900
tcacaggaga tgctccctac acgctgcagg aaagtccagt gcctgcagca caggcttcag  15960
cagcagactc gggttctagt ctcagtctgc tgattcctag ttgtggaacc tgagcaggcg  16020
aagttactaa acctctctgt gcgtcagcct cccaggctcg ttgcttcagg ccgcagttag  16080
gctgtgtgaa caggagagtg gggatgggaa ctaggtatct taaagcgggg cagagtttgg  16140
atgagcgggc caccccttcgt atagttagga ggaagatgac gggaggcatg gaagctggga  16200
tagccatcct gagtcagtgc taattctgac acttcagaac atcgagtcag tctgacctgc  16260
```

-continued

```
gagtgagctt tcattgacca cttagaaact attagcacct tggacaaact actttctttc  16320
agacctggtt gcttcatgtc tgcgatggga aaactgatac ttaacttgca gatagtggtg  16380
aatcaaaagt agtatatgtg aagtactcac acactgcgga gcattcagcc atcgtcccat  16440
cctacttcta ccttttacat attgtaatat gaaagctaaa ccatttctcg atgtgagtca  16500
gttttaatcg gctacatagt gagtggcatt cgattttaaa aatgtcaact tgggatctgt  16560
caccatgcta cttaccattt gtatgtcaca ctgtttgaat gtcggacctg gtttgttttt  16620
ctccagatgg tatgttactt acggtcatga actgatttgg aagaacaggg agccgctagt  16680
gaaaatctgg catgaaataa ggactaatgg ccccaaaaaa ggaggtggct ctaagtaaaa  16740
ctgggattgg acagtagtgg tgcatctggt ccttgccgcc tgagagcccc aggagacatc  16800
ggctagagtg accatggcta tgctcccgtc tggaagatgc cagcatctgg cctcccactg  16860
ttttcagctg tgtcccccag tccgtgtctt tttagaatgt gaatgatgat aaagttgtga  16920
aataaaggtt tctatctagt ttgtaagcag atgtgtgtgt tctctcttta aggggccgac  16980
acggctctgg cattttgctt tggttgttgc attgacagga cctggggaga gtgcaccctg  17040
aaaggcctga tcagaacatg aaggcgctgg ttgcctgtct ttggaccctc cagtgcctct  17100
gcttagcctt cactcttcct tgcctccccc tcccctgggt tggctgcaca taaaagtcaa  17160
gagtatcccc tctccagcac aatctgaaat aacagctgca gtattttctc aattttcagg  17220
aaaggtagtg ttttctggca gtgagtggca tatacaaaaa gctattttca ggttttgctt  17280
tctaggttca atttgtagat aaattaagag gtagaaagaa gtgatttggg taaattcaga  17340
cttgaaatct gagccgaatt ttatcttctg tttgaaagtg ttctaattga agcgtctcac  17400
tgaaaatagc agatagtggc tgtcgtcgtc acagccctca ctgttgtgga attcatgtta  17460
ccctcgtgac tgagaatgac atctaggaaa tgcagtttga gagtatgttc ttcttgaagt  17520
catttacagg agaattttta gtcttttgat ggcttcaaaa tgttatacca agtcttgcag  17580
ctttgtcctg ggaggatcga aggccctgat ttcagcctcc tgtggccgat cggactcagg  17640
ttgtgtgccg tgggggatgg gaatggcggc tttggaaaag gagtgggagt ggtgcccacc  17700
tcaccaggca agtgagaact gcatggcagc acgcgcccag cacatagaaa ttgtccagta  17760
tttggcagtc cttcatatcc ttcttccatc aggctggact tgtttctact atgatttaca  17820
gttattcttc ccaggcacag gattctgttc taaactcgta tcacttctag gggagagagt  17880
tatcttagcc atcattttgc cagcgaggaa acggcacacg tggtgtaggg gcactgccca  17940
aggtcacaat gctttgctct gacatctgct aacaactgca acacagatga ggcaagatgc  18000
gttttccaga gatgggatag gaggctgagt tcatagggac attccctcta gagcccaaca  18060
ttaattcaca tcgtgctttg ggcagaccag gcaaagaggc aatgaagaca tctctgtgtc  18120
cctgctttgt gactgggaaa aagttagaag tccctgtagc atctcctggt ccctaaaacc  18180
cctcaatgct ggagcctctg tgcatggcct ggggaggcca gaacctggct gtggccggag  18240
aagccttgct gtccacagct ccctcctgat tgcccacgag ggtgcttcac tttctcctct  18300
tggcttctct ggggacccgc gatcactgcc ttcaaggcca tgcactccct ggcccgtggg  18360
cctcttgggc tgtgccgcct ccactggcat ctgaagtgtg gggtacctag gaacatgccg  18420
tggctgccgt ctccctcatt ccatacactt cttgagtggg tgcacttgct gaagcctcag  18480
ttatctgtga ggattctgag ctccagaccc acagaatctc tctgtactct tagtaaatgt  18540
gtctactgca acacacgcat ggttccaggc tctgggacca ccccccgcc ctgcacaggc  18600
ccctcaaata gcactcggct taaggagtga cacgagcaat cggtgaagtc tgaaacccgg  18660
```

-continued

```
agccattcga gatctccctc tctcgcctct tatttctaga attcagcccc tcagccttcc  18720

cagtgcctgt gactccgtgg tggtcctcac ttcttagtcc ctggactgtt gagcctgttc  18780

ttccagctgg tctccaaagc aaccctgtgc ttctccatat gcctgccaga gtgctaaaaa  18840

cacgtctgtc attcctttgt tgtcacctgt gaaaaacttt tatttatttg agacagggtc  18900

tctctctctc tctctcgtcc aggctggagt tcagtggtgc aatctagatg gtcactacac  18960

tcagggagtt ggggatggct cagagctgtt aacagagagg ggactgccca ggaggacctg  19020

cgtgaggggt gggggtggga tgacaaggaa ccagctctgg gagttgaaag acctggattc  19080

aagtctcaac ccaagccctg gccagctctg ggaccccgga caagtcggcc tcactctctg  19140

cccctcagtg ggctcctgtg tagatgggga taatgatggc tttatatcct gagaatgtgg  19200

ggaggggatt aagtggccaa aatacctgag agtgcgcact cagtgcctgg ctcagcaaat  19260

gcccttgttc cctccttccc tctccccaga acccctcctc cccttcttct tctttttttt  19320

tttttttttt tgacccagag tcttgctatg ttgcccaggc tggagtgcag tggcacaatc  19380

tcggctcact gcaacctcca cctcctggct tcaggcaatt cttgtgcctc agcctctcga  19440

gtagctggga ttacaggcag gcaccatcac gcccggctaa tttttttttt ttttttttgt  19500

agtagaaatg ggatttcacc atattggcag gatgttctcg atctcctgac ctcaggtgat  19560

ccactcgcct tggcctccca aagtgctggg attataggtg tcagccactg cgcccagccc  19620

ccattgttta tctcctcttc catttcttgt ggggactttt aaaggaaaaa tcaggttggt  19680

gggctggggg agggcatagc tgagaccacc ttgagggcac caagctcact gaccac      19736
```

<210> SEQ ID NO 4
<211> LENGTH: 379
<212> TYPE: PRT
<213> ORGANISM: Human

<400> SEQUENCE: 4

```
Met Ala Trp Arg Gly Trp Ala Gln Arg Gly Trp Gly Cys Gly Gln Ala
 1               5                  10                  15

Trp Gly Ala Ser Val Gly Gly Arg Ser Cys Glu Glu Leu Thr Ala Val
            20                  25                  30

Leu Thr Pro Pro Gln Leu Leu Gly Arg Arg Phe Asn Phe Phe Ile Gln
        35                  40                  45

Gln Lys Cys Gly Phe Arg Lys Ala Pro Arg Lys Val Glu Pro Arg Arg
    50                  55                  60

Ser Asp Pro Gly Thr Ser Gly Glu Ala Tyr Lys Arg Ser Ala Leu Ile
65                  70                  75                  80

Pro Pro Val Glu Glu Thr Val Phe Tyr Pro Ser Pro Tyr Pro Ile Arg
                85                  90                  95

Ser Leu Ile Lys Pro Leu Phe Phe Thr Val Gly Phe Thr Gly Cys Ala
            100                 105                 110

Phe Gly Ser Ala Ala Ile Trp Gln Tyr Glu Ser Leu Lys Ser Arg Val
        115                 120                 125

Gln Ser Tyr Phe Asp Gly Ile Lys Ala Asp Trp Leu Asp Ser Ile Arg
    130                 135                 140

Pro Gln Lys Glu Gly Asp Phe Arg Lys Glu Ile Asn Lys Trp Trp Asn
145                 150                 155                 160

Asn Leu Ser Asp Gly Gln Arg Thr Val Thr Gly Ile Ile Ala Ala Asn
                165                 170                 175

Val Leu Val Phe Cys Leu Trp Arg Val Pro Ser Leu Gln Arg Thr Met
```

-continued

```
            180                 185                 190

Ile Arg Tyr Phe Thr Ser Asn Pro Ala Ser Lys Val Leu Cys Ser Pro
        195                 200                 205

Met Leu Leu Ser Thr Phe Ser His Phe Ser Leu Phe His Met Ala Ala
    210                 215                 220

Asn Met Tyr Val Leu Trp Ser Phe Ser Ser Ser Ile Val Asn Ile Leu
225                 230                 235                 240

Gly Gln Glu Gln Phe Met Ala Val Tyr Leu Ser Ala Gly Val Ile Ser
                245                 250                 255

Asn Phe Val Ser Tyr Leu Gly Lys Val Ala Thr Gly Arg Tyr Gly Pro
            260                 265                 270

Ser Leu Gly Ala Ser Gly Ala Ile Met Thr Val Leu Ala Ala Val Cys
        275                 280                 285

Thr Lys Ile Pro Glu Gly Arg Leu Ala Ile Ile Phe Leu Pro Met Phe
    290                 295                 300

Thr Phe Thr Ala Gly Asn Ala Leu Lys Ala Ile Ile Ala Met Asp Thr
305                 310                 315                 320

Ala Gly Met Ile Leu Gly Trp Lys Phe Phe Asp His Ala Ala His Leu
                325                 330                 335

Gly Gly Ala Leu Phe Gly Ile Trp Tyr Val Thr Tyr Gly His Glu Leu
            340                 345                 350

Ile Trp Lys Asn Arg Glu Pro Leu Val Lys Ile Trp His Glu Ile Arg
        355                 360                 365

Thr Asn Gly Pro Lys Lys Gly Gly Gly Ser Lys
    370                 375
```